United States Patent
Cheng et al.

(10) Patent No.: US 8,183,249 B2
(45) Date of Patent: May 22, 2012

(54) INHIBITORS OF AKT/PKB WITH ANTI-TUMOR ACTIVITY

(75) Inventors: Jin Q. Cheng, Tampa, FL (US); Mei Sun, Tampa, FL (US); Said M. Sebti, Tampa, FL (US)

(73) Assignee: University of South Florida, Tampa, FL (US)

( * ) Notice: Subject to any disclaimer, the term of this patent is extended or adjusted under 35 U.S.C. 154(b) by 758 days.

(21) Appl. No.: 12/172,831

(22) Filed: Jul. 14, 2008

(65) Prior Publication Data
US 2009/0028855 A1    Jan. 29, 2009

Related U.S. Application Data

(60) Provisional application No. 60/949,365, filed on Jul. 12, 2007.

(51) Int. Cl.
*A61K 31/517* (2006.01)
*C07D 471/00* (2006.01)

(52) U.S. Cl. .................. 514/266.2; 514/266.1; 544/278; 544/279

(58) Field of Classification Search .................. 544/278, 544/279; 514/266.1, 266.2
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,167,649 A | 12/1992 | Zook | |
| 7,081,449 B2 | 7/2006 | Pietrzkowski et al. | |
| 2004/0063658 A1 | 4/2004 | Roberts et al. | |

FOREIGN PATENT DOCUMENTS

| | | |
|---|---|---|
| WO | 0203997 | 1/2002 |
| WO | 03093290 | 11/2003 |

OTHER PUBLICATIONS

Anderson et al., Journal of Organic Chemistry (1977), 42(6), 997-1000.*
Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.TheOncologist.com].*
Kim, D., et al., "A Small Molecule Inhibits Akt through Direct Binding to Akt and Preventing Akt Membrane Translocation," Journal of Biological Chemistry (2010), 285(11), 8383-8394.
Pietrzkowski, Z., et al., "Synthesis and anticancer activity of 4-amino-5-oxo-8-(β-D-xylofuranosyl)pyrido[2,3-d] pyrimidine," Nucleosides, Nucleotides & Nucleic Acids (2001), 20(4-7), 323-328.
Girardet, J., et al., "Synthesis and Cytotoxicity of 4-Amino-5-oxopyrido[2,3-d]pyrimidine Nucleosides," Journal of Medicinal Chemistry (2000), 43(20), 3704-3713.
Anderson, G., et al., "Pyridopyrirnidines. 7. Ribonucleosides structurally related to the antitumor antibiotic sangivamycin," Journal of Organic Chemistry (1977), 42(6), 997-1000.
Rizkalla, B., et al., "Pyrido[2,3-d]pyrimidines. III. Synthesis of some 8-β-D-ribofuranosylprido[2,3-d]pyrimidines structurally related to the antibiotic sangivamycin," Journal of Organic Chemistry (1972), 37(25), 3980-5.
Bailey HH, Mahoney MR, Ettinger DS, et al. (2006) Phase II study of daily oral perifosine in patients with advanced soft tissue sarcoma. Cancer, 107:2462-7.
Bellacosa A, Chan TO, Ahmed NN, et al. (1998) Akt activation by growth factors is a multiple-step process: the role of the PH domain. Oncogene, 17:313-25.
Bellacosa A, Testa JR, Staal SP, Tsichlis PN. (1991) A retroviral oncogene, akt, encoding a serine-threonine kinase containing an SH2-like region. Science, 254: 274-7.
Carpten JD, Faber AL, Horn C, et al. (2007) A transforming mutation in the pleckstrin homology domain of AKT1 in cancer. Nature; [Epub ahead of print] .
Casamayor A, Morrice NA, Alessi DR. (1999) Phosphorylation of Ser-241 is essential for the activity of 3-phosphoinositide-dependent protein kinase-1: identification of five sites of phosphorylation in vivo. Biochem J, 342:287-92.
Castillo SS, Brognard J, Petukhov PA, et al. (2004) Preferential inhibition of Akt and killing of Akt-dependent cancer cells by rationally designed phosphatidylinositol ether lipid analogues. Cancer Res, 64:2782-92.
Cheng JQ and Nicosia SV. (2001) AKT signal transduction pathway in oncogenesis. In: Schwab D, editor. Encyclopedic Reference of Cancer. Berlin Heidelberg and New York: Springer; p. 35-7.
Cheng JQ, Altomare DA, Klein MA, et al. (1997) Transforming activity and cell cycle-dependent expression of the AKT2 oncogene: evidence for a link between cell cycle regulation and oncogenesis. Oncogene, 14:2793-801.
Cheng JQ, Godwin AK, Bellacosa A, et al. (1992) A putative oncogene encoding a member of a subfamily of protein-serine/threonine kinases, is amplified in human ovarian carcinomas. Proc Natl Acad Sci USA, 89:9267-71.
Cheng JQ, Lindsley CW, Cheng GZ, Yang H, Nicosia SV. (2005) The Akt/PKB pathway: molecular target for cancer drug discovery. Oncogene, 24:7482-92.
Cheng JQ, Ruggeri B, Klein WM, et al. (1996) Amplification of AKT2 in human pancreatic cells and inhibition of AKT2 expression and tumorigenicity by antisense RNA. Proc Natl Acad Sci USA, 93:3636-41.
Datta SR, Brunet A, Greenberg ME. (1999) Cellular survival: a play in three Akts. Genes Dev, 13:2905-27.
Feng J, Park J, Cron P, Hess D, Hemmings BA. (2004) Identification of a PKB/Akt hydrophobic motif Ser-473 kinase as DNA-dependent protein kinase. J Biol Chem, 279: 41189-96.

(Continued)

*Primary Examiner* — Paul V. Ward
(74) *Attorney, Agent, or Firm* — Klauber & Jackson LLC

(57) ABSTRACT

The subject invention concerns materials and methods for inhibiting the Akt/PKB pathway. In one embodiment, a compound of the invention inhibits kinase activity and/or phosphorylation levels of Akt proteins. The subject invention also concerns methods for inhibiting or killing a cancer cell or other cell in which expression of an Akt protein is elevated or constitutively active, comprising contacting the cell with an effective amount of a compound of formula I. The subject invention also concerns methods for treating cancer or a tumor in a person or animal comprising administering an effective amount of a compound of formula I to the person or animal.

16 Claims, 18 Drawing Sheets

OTHER PUBLICATIONS

Feun LG, Blessing JA, Barrett RJ, Hanjani P. (1993) A Phase II trial of tricyclic nucleoside phosphate in patients with advanced squamous cell carcinoma of the cervix: a Gynecologic Oncology Group study. Am J Clin Oncol, 16: 506-8.

Granville CA, Memmott RM, Gills JJ, Dennis PA. (2006) Handicapping the race to develop inhibitors of the phosphoinositide 3-kinase/Akt/mammalian target of rapamycin pathway. Clin Cancer Res, 12:679-89.

Greene, T.W. and Wuts, P.G.M. "Protective Groups in Organic Synthesis" John Wiley & Sons, Inc. New York. 3rd Ed. p. 819, 1999.

Hoffman K, Holmes FA, Fraschini G, et al. (1996) Phase I-II study: triciribine (tricyclic nucleoside phosphate) for metastatic breast cancer. Cancer Chemother Pharmacol., 37:254-8.

Honda, T. et al. Bioorg. Med. Chem. Lett., 1997, 7:1623-1628.

Honda, T. et al. Bioorg. Med. Chem. Lett., 1998, 8:2711-2714.

Honda, T. et al. J. Med. Chem., 2000, 43:4233-4246.

Jetzt A, Howe JA, Horn MT, et al. (2003) Adenoviral-mediated expression of a kinase-dead mutant of Akt induces apoptosis selectively in tumor cells and suppresses tumor growth in mice. Cancer Res, 63:697-706.

Jiang K, Coppola D, Crespo NC, et al. (2000) The phosphoinositide 3-OH kinase/AKT2 pathway as a critical target for farnesyltransferase inhibitor-induced apoptosis. Mol Cell Biol, 20:139-48.

Jin X, Gossett DR, Wang S, et al. (2004) Inhibition of AKT survival pathway by a small molecule inhibitor in human endometrial cancer cells. Br J Cancer, 91:1808-12.

Jones PF, Jakubowicz T, Pitossi FJ, Maurer F, Hemmings BA. (1991a) Molecular cloning and identification of a serine/threonine protein kinase of the second-messenger subfamily. Proc Natl Acad Sci USA, 88:4171-5.

Jones PF, Jakubowicz T, Hemmings BA. (1991b) Molecular cloning of a second form of rac protein kinase. Cell Reg, 2:1001-9.

Kondapaka SB, Singh SS, Dasmahapatra GP, Sausville EA, Roy KK. (2003) Perifosine, a novel alkylphospholipid, inhibits protein kinase B activation. Mol Cancer Ther, 2:1093-103.

Konishi H, Kuroda S, Tanaka M, et al. (1995) Molecular cloning and characterization of a new member of the Rac protein kinase family: association of the pleckstrin homology domain of three types of Rac protein kinase with protein kinase C subspecies and beta gamma subunits of G proteins. Biochem Biophys Res Commun, 216:526-34.

Konoike, T. et al. J. Org. Chem., 1997, 62:960-966.

Lindsley CW, Zhao Z, Leister WH, et al. (2005) Allosteric Akt (PKB) inhibitors: discovery and SAR of isozyme selective inhibitors. Bioorg Med Chem Lett, 15:761-4.

Luo Y, Shoemaker AR, Liu X, et al. (2005) Potent and selective inhibitors of Akt kinases slow the progress of tumors in vivo. Mol Cancer Ther, 4:977-86.

Marsh Rde W, Rocha Lima CM, Levy DE, Mitchell EP, Rowland KM Jr, Benson AB 3rd. (2007) A phase II trial of perifosine in locally advanced, unresectable, or metastatic pancreatic adenocarcinoma. Am J Clin Oncol, 30:26-31.

Martin, E.W., 1995, Remington, 19th ed., Easton Pennsylvania, Mack Publishing Company.

Meuillet EJ, Ihie N, Baker AF, et al. (2004) in vivo molecular pharmacology and antitumor activity of the targeted Akt inhibitor nhibitor PX-316. Oncol Res, 14:513-27.

Persad S, Attwell S, Gray V, et al. (2001) Regulation of protein kinase B/Akt-serine 473 phosphorylation by integrin-linked linked kinase: critical roles for kinase activity and amino acids arginine 211 and serine 343. J Biol Chem, 276:27462-9.

Sarbassoy DD, Guertin DA, Ali SM, Sabatini DM. (2005) Phosphorylation and regulation of Akt/PKB by the rictor-mTOR complex. Science, 307:1098-101.

Sato S, Fujita N, Tsuruo T. (2002) Interference with PDK1-Akt survival signaling pathway by UCN-01 (7-hydroxystaurosporine). Oncogene, 21:1727-38.

Solit DB, Basso AD, Olshen AB, Scher HI, Rosen N. (2003) Inhibition of heat shock protein 90 function down-regulates Akt kinase and sensitizes tumors to Taxol. Cancer Res, 63: 2139-44.

Stambolic V, Suzuki A, de la Pompa JL, et al. (1998) Negative regulation of PKB/Akt-dependent cell survival by the tumor suppressor PTEN. Cell, 95:29-39.

Sun J, Blaskovich MA, Knowles D, et al. (1999) Antitumor efficacy of a novel class of non-thiol-containing peptidomimetic inhibitors of farnesyltransferase and geranylgeranyltransferase I: combination therapy with the cytotoxic agents cisplatin, Taxol, and gemcitabine. Cancer Res, 59:4919-26.

Sun M, Wang G, Paciga JE, et al. (2001) AKT1/PKB•kinase is frequently elevated in human cancers and its constitutive activation is required for oncogenic transformation in NIH3T3 cells. Am J Path, 159:431-7.

Toker A and Newton AC. (2000) Akt/Protein kinase B is regulated by autophosphorylation at the hypothetical PDK-2 Site. J Biol Chem, 275:8271-4.

Van Ummersen L, Binger K, Volkman J, et al. (2004) A phase I trial of perifosine (NSC 639966) on a loading dose/maintenance dose schedule in patients with advanced cancer. Clin Caner Res, 10:7550-6.

Vazquez F, Sellers WR. (2000) The PTEN tumor suppressor protein: an antagonist of phosphoinositide 3-kinase signaling. Biochim Biophys Acta, 1470:M21-35.

West KA, Castillo SS and Dennis PA. (2002) Activation of the PI3K/Akt pathway and chemotherapeutic resistance. Drug Resist Updat, 5:234-48.

Wick MJ, Dong LQ, Riojas RA, Ramos FJ, Liu F. (2000) Mechanism of phosphorylation of protein kinase B/Akt by a constitutively active 3-phosphoinositide-dependent protein kinase-1. J Biol Chem, 275:40400-6.

Xu W, Yuan X, Jung YJ, et al. (2003) The Heat Shock Protein 90 Inhibitor Geldanamycin and the ErbB inhibitor ZD1839 promote rapid PP1 phosphatase-dependent inactivation of AKT in ErbB2 overexpressing breast cancer cells. Cancer Res, 63:7777-84.

Yang L, Dan HC, Sun M, et al. (2004) Akt/protein kinase B signaling inhibitor-2, a selective small molecule inhibitor of Akt signaling with antitumor activity in cancer cells overexpressing Akt. Cancer Res, 64:4394-9.

Yang WL, Roland IH, Godwin AK, Xu XX. (2005) Loss of TNF-alpha-regulated COX-2 expression in ovarian cancer cells. Oncogene, 24:7991-8002.

* cited by examiner

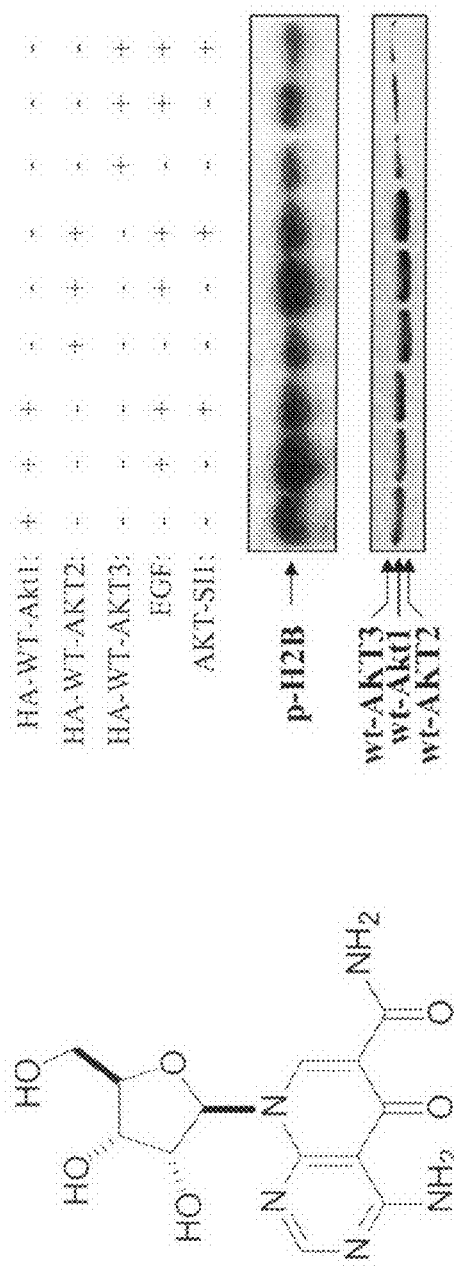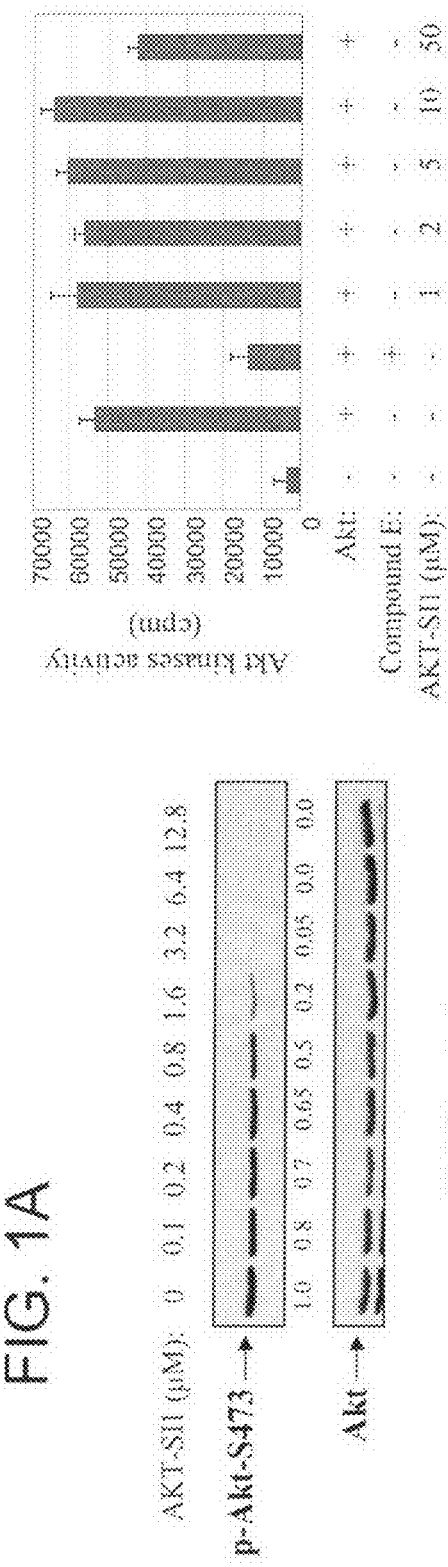

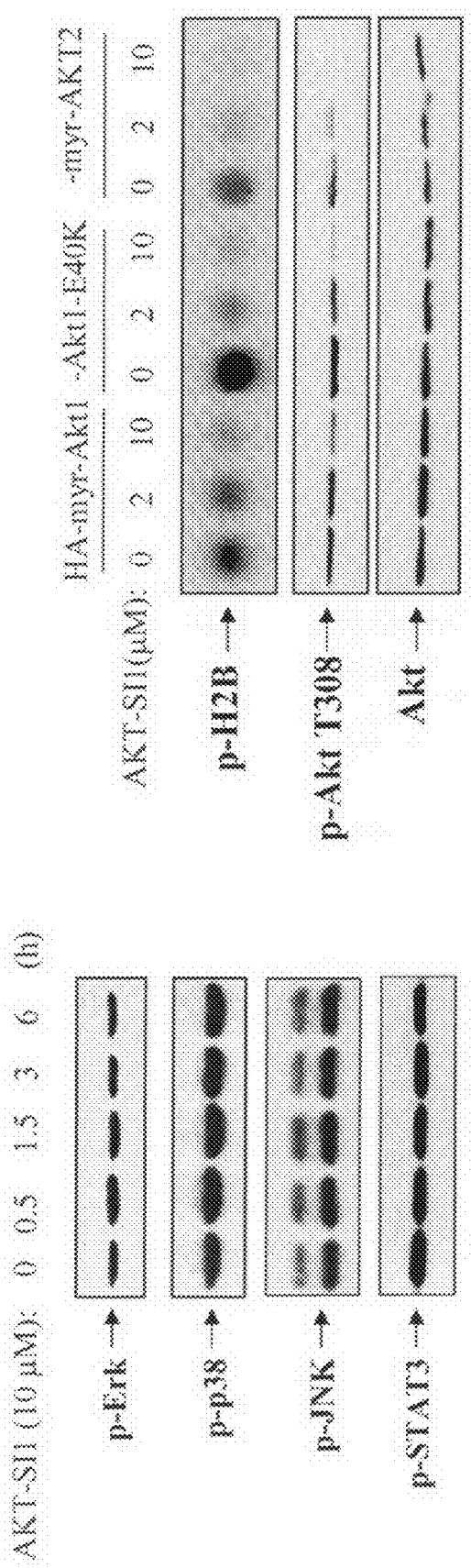

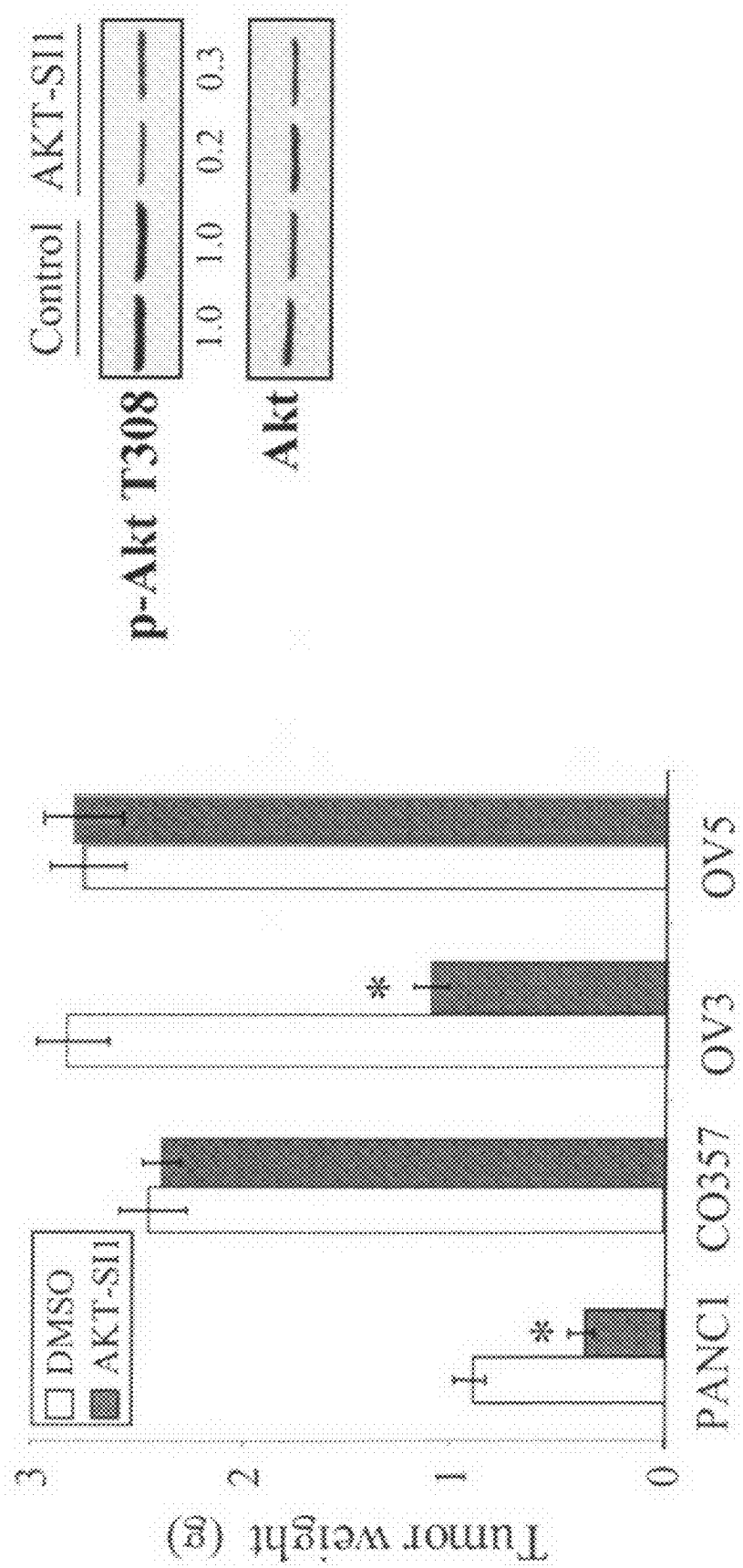

INHIBITORS OF AKT/PKB WITH ANTI-TUMOR ACTIVITY

CROSS-REFERENCE TO RELATED APPLICATION

The present application claims the benefit of U.S. Provisional Application Ser. No. 60/949,365, filed Jul. 12, 2007, which is hereby incorporated by reference herein in its entirety, including any figures, tables, nucleic acid sequences, amino acid sequences, and drawings.

GOVERNMENT SUPPORT

The subject matter of this application has been supported by a research grants from the National Institutes of Health-National Cancer Institute and ARMY/MRMC under grant numbers R01CA107078, DAMD17-02-1-0671, and W81XWH-05-1-0021. Accordingly, the government has certain rights in this invention.

BACKGROUND OF THE INVENTION

Akt, also called protein kinase B, represents a subfamily of the serine/threonine kinase. Akt was first described as the cellular homologue of the product of the v-akt oncogene (Bellacosa et al. 1991), and it has three members, Akt1/PKBα, Akt2/PKBβ and Akt3/PKBγ (Cheng et al. 1992; Jones et al. 1991a; Jones et al. 1991b). Activation of Akt depends on the integrity of the pleckstrin homology (PH) domain, which mediates its membrane translocation, and on the phosphorylation of Thr$^{308}$ in the activation loop and Ser$^{473}$ (Konishi et al. 1995). Phosphoinositides, PtdIns-3,4-P2 and PtdIns-3,4,5-P3, produced by PI3 K bind directly to the PH domain of Akt, driving a conformational change in the molecule, which enables the activation loop of Akt to be phosphorylated by PDK1 at Thr$^{308}$ (Datta et al. 1999). Full activation of Akt is also associated with phosphorylation of Ser$^{473}$ within a C-terminal hydrophobic motif (Datta et al. 1999). Although the role of PDK1 in Thr$^{308}$ phosphorylation is well established, the mechanism of Ser$^{473}$ phosphorylation is controversial. A number of candidate enzymes responsible for this modification have been put forward, including integrin-linked kinase (Persad et al. 2001), PDK1 when in a complex with the kinase PRK2 (Wick et al. 2000), Akt itself, through autophosphorylation (Toker et al. 2000), DNA-dependent kinase (Feng et al. 2004), and the rictor-mTOR complex (Sarbassoy et al. 2005). The activity of Akt is negatively regulated by tumor suppressor PTEN, which is frequently mutated in human malignancy (Vazquez et al. 2000). PTEN encodes a dual-specificity protein and lipid phosphatase that reduces intracellular levels of PtdIns-3,4,5-P3 by converting them to PtdIns-4,5-P2, thereby inhibiting the PI3K/Akt pathway (Stambolic et al. 1998).

Akt phosphorylates and/or interacts with a number of molecules to exert its normal cellular functions, which include roles in cell proliferation, survival, migration and differentiation (Cheng et al. 2001). Many lines of evidence demonstrate that Akt is a critical player in the tumor development and progression. In addition, aberrant hyperactivation of Akt pathway has been detected in up to 50% all human tumors (Sun et al. 2001; Cheng et al. 1997) and is closely associated with chemoresistance (West et al. 2002). Therefore, Akt has been an attracting target for anti-cancer drug discovery (West et al. 2002).

In the last several years, through combinatorial chemistry, high-throughput and virtual screening, and traditional medicinal chemistry, a dozen inhibitors of the Akt pathway have been identified. Lipid-based inhibitors of Akt were the first to be developed, including perifosine (Kondapaka et al. 2003), PX-316 (Meuillet et al. 2004) and phosphatidylinositol ether lipid analogues (Castillo et al. 2004), which were designed to interact with the PH domain of Akt. In addition, several Akt antagonists have been identified using high-throughput screening of chemical libraries and rational design. These inhibitors include 9-methoxy-2-methylellipticinium acetate (Jin et al. 2004), the indazole-pyridine A-443654 (Luo et al. 2005), isoform-specific allosteric kinase inhibitors (Lindsley et al. 2005) and Akt/PKB signaling inhibitor-2 (API-2), also called triciribine/TCN (Yang et al. 2004). API-2/TCN is a tricyclic nucleoside that previously showed antitumor activity in phase I and phase II trials conducted, but multiple toxicities, including hepatotoxicity, hyperglycemia, thrombocytopenia, and hypertriglyceridemia, precluded further development (Feun et al. 1993; Hoffman et al. 1996). By screen of the NCI diversity set, we have previously shown that API-2 inhibit Akt kinase activity and stimulate apoptosis of xenografts of human cancer cells exhibiting high Akt activity (Yang et al. 2004). This finding has provided new interest in studying this drug and raises the possibility that lower doses may inhibit Akt and induce tumor cell apoptosis without the previously associated side effects (Yang et al. 2004; Cheng et al. 2005).

BRIEF SUMMARY OF THE INVENTION

The subject invention concerns compounds, compositions, and methods for inhibiting the Akt/PKB pathway. In one embodiment, a compound of the invention inhibits kinase activity and/or phosphorylation levels of Akt proteins. Compounds of the invention have the general structure shown in formula I. In a specific embodiment, a compound of the invention (referred to herein as API-1) has the structure:

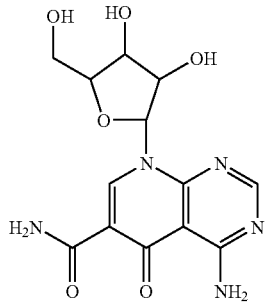

Compounds of the invention, such as API-1, inhibit Akt signaling in human tumor cells with aberrant Akt leading to inhibition of cell growth and induction of apoptosis. In a xenograft nude mice model, compounds of the invention considerably inhibit tumor growth in the cells with hyperactivated Akt but not in the tumors with low levels of Akt.

The subject invention also concerns methods for inhibiting or killing a cancer cell or other cell in which expression of an Akt protein is elevated or constitutively active, comprising contacting the cell with an effective amount of a compound of formula I.

The subject invention also concerns methods for treating cancer or a tumor in a person or animal comprising administering an effective amount of a compound of formula I to the person or animal.

The serine/threonine kinase Akt/PKB pathway is frequently hyperactivated in human cancer and functions as a cardinal nodal point for transducing extracellular and intracellular oncogenic signals, and thus it presents a target for molecular therapeutics. By screening the National Cancer Institute Diversity Set, a small molecule Akt pathway inhibitor, APT (Akt/PKB signaling inhibitor)-1, was identified.

API-1 inhibits the kinase activity and phosphorylation level of three members of Akt family. However, it had no the effects on the activity of the upstream activators, PI3K and PDK1. Further, the kinase activity and phosphorylation levels of constitutively active Akt were largely inhibited by API-1 in cell culture, while it had no effect on Akt kinase activity in vitro. API-1 is highly selective for Akt and does not inhibit the activation of PKC, SGK, PKA, STAT3, Erk-1/2, or JNK. The inhibition of Akt by API-1 resulted in induction of cell growth arrest and apoptosis in human cancer cells that harbor constitutively activated Akt. Significantly, API-1 selectively inhibited tumor growth in nude mice of human cancer cells in which Akt is elevated but not of those cancer cells in which it is not. These data suggest that API-1 is an Akt pathway inhibitor with anti-tumor activity in vitro and in vivo and could be a potential anti-cancer agent for patients with cancer expressing hyperactivated Akt.

Akt is a major pathway regulating cancer cell survival, growth and tumor progression. It has been well documented that elevated levels of Akt kinase contribute to resistance to various cancer therapies, including cell-toxic chemotherapeutic drugs and small molecule inhibitors of Bcr-Abl (Gleevec), Her2/Neu (Hercptin), and mTOR (rapamycin). Blocking Akt inhibits tumor growth in the cancer cells with hyperactivated Akt and renders cancer cells more sensitive to chemotherapy and other targeted therapies. Combination of API-1 with other anti-tumor drugs provides more potent anti-tumor effects.

BRIEF DESCRIPTION OF THE DRAWINGS

FIGS. 1A-1D are graphical representations of the identification of API-1 as a candidate of Akt inhibitor from the NCI Diversity Set. FIG. 1A shows the chemical structure of API-1. FIG. 1B is a graph showing that API-1 inhibits three members of Akt. HEK293 cells were transfected with HA-Akt1, -AKT2 and -AKT3 and treated with API-1 (10 μM) prior to EGF stimulation, the cells were lysed and immunoprecipitated with anti-HA antibody. The immnunoprecipitates were subjected to in vitro kinase assay (top). Bottom panel is a Western blot showing expression of transfected Akt1, AKT2 and AKT3 detected with anti-HA antibody. FIG. 1C is a graph showing that API-1 inhibits phosphorylation levels of Akt in OVCAR3 cells, which express hyperactivated Akt. The cells were treated with API-1 at indicated concentration for 2 hours and subjected to immunoblotting analysis with anti-phospho-Akt-S473 antibodies (top panel). Bottom panel shows expression of total Akt. FIG. 1D is a graph showing that APT-1 did not inhibit Akt in vitro. In vitro kinase assay of recombinant constitutively active Akt protein in a kinase buffer containing indicated amount of API-1. Compound E, an ATP-competitor of multiple kinase inhibitors, was used as positive control. The experiment was repeated three times.

FIGS. 2A-2G are graphs showing that API-1 does not inhibit PI3K, PDK1 and the closely related members of AGC kinase family. FIG. 2A is a graph showing in vitro PI3K kinase assay. HEK293 cells were serum-starved and treated with APT-1 (10 μM) or Wortmannin (1 nM) for 30 minutes prior to EGF stimulation. Cells were lysed and immunoprecipitated with anti-p110α antibody. The immunoprecipitates were subjected to in vitro kinase assay using PI-4-P as substrate. FIG. 2B is a graph showing the effect of API-1 on PDK1 activation. In vitro kinase assay was performed with PDK1 kinase kit (Upstate Biotechnology Inc) according to manufacture's instruction in the presence of indicated compounds. FIG. 2C is a graph showing in vitro PKA kinase assay. Recombinant PKA was incubated in ADB buffer (Upstate Biotechnology Inc) containing indicated inhibitors (API-1 or PKAI) and substrate Kemptide. The kinase activity was quantified. FIG. 2D is a graph showing the effect of API-1 on PKA, PKC and PDK kinase activity in living cells. OVCAR3 cells were treated with indicated concentration of API-1 for 1 hour. Cells were lysed and immunoblotted with indicated antibodies. FIG. 2E is a graph showing in vitro SGK kinase assay. Recombinant SGK protein was incubated with API-1 or compound E. Kinase assay was started by adding SGK substrate peptide and $[\gamma\text{-}^{32}P]$ ATP. The kinase activity was quantified. FIG. 2F is a graph showing the results when HEK293 cells were transfected with HA-SGK and treated with API-1 or Wortmannin prior to EGF stimulation. In vitro kinase was performed with HA-SGK immunoprecipitates using histone-H2B as substrate. FIG. 2G is a graph showing that API-1 does not inhibit phosphorylation of Erk, p38, JNK and Stat3. OVCAR3 cells were treated with APT-1 for 3 hours and immunioblotted with indicated antibodies.

FIGS. 3A-3D are graphs demonstrating that API-1 inhibits constitutively active Akt and its downstream targets. FIG. 3A is a graph demonstrating that API-1 inhibits constitutively active Akt. HEK293 cells were transfected with indicated HA-myr-Akt1, HA-Akt1-E40K and HA-myr-Akt2. Following treatment with API-1 for 1 hour, cells were lysed and immunoprecipitated with anti-HA antibody. The immunoprecipitates were subjected to in vitro kinase assay (top panel) and immunoblotting with indicated antibodies (middle and bottom panels). FIG. 3B is a graph demonstrating that API-1 inhibits phosphorylation of Akt downstream targets. OVCAR3 cells were treated with API-1 (10 μM) for indicated times and immunoblotted with indicated antibodies. API-1 significantly reduces the phosphorylation levels of Akt and its downstream targets, GSK3β and S6 protein. In FIG. 3C, AKT-SI1 inhibited phosphorylation of Akt downstream targets. In FIG. 3D. AKT-SI1 did not interfere with mTORC1 and mTORC2 complexes.

FIG. 4A is a Western blot showing the results following treatment with API-1, phosphorylation levels of Akt and PARP cleavage were detected with anti-phospho-Akt-T308 and cleaved PARP antibodies in indicated human cancer cell lines (top and middle panels). The blots were reprobed with anti-actin antibody (bottom panel). FIGS. 4B and 4C are cell proliferation assays in which indicated cell lines were treated with different doses of API-1 for 24 hours and then analyzed with MTT assay. FIGS. 4D-4G show an apoptosis analysis in which cells were treated with API-1 and stained with annexin V and PI and analyzed by FACScan.

FIGS. 5A-5L are graphics demonstrating that API-1 exhibits anti-tumor activity in cancer cell lines with elevated Akt in mouse xenograft. FIGS. 5A-5F are photos of the control (FIG. 5A) and API-1-treated groups (FIG. 5B) and the related graphs (FIGS. 5C-5F). Tumor cells were subcutaneously injected into nude mice with low level of Akt cells on right side and elevated level of Akt cells on left side. When the tumors reached an average size of about 100-150 mm$^3$, animals were treated with either vehicle or 10 mg/kg/day API-1 as described in "Materials and Methods." Representation of the mice with PANC1/OVCAR3 (FIGS. 5E and 5C, respectively), which express elevated levels of Akt, and COLO357/OVCAR5 (FIGS. 5F and 5D, respectively), which exhibit low levels of Akt, xenografts treated with API-1 or vehicle (A). Panel B shows tumor growth curve with 10 mice/group. FIGS. 5G-5J show examples of tumor size (left) and weight (right) at the end of experiment. API-1 significantly reduced tumor weight in PANC1 and OVCAR3 xenografts (*P≦0.02) as compared to DMSO control. FIGS. 5K and 5L demonstrate that API-1 inhibits Akt phosphorylation in vivo. API-1 treated and untreated tumor specimens were lysed and immunoblotted with indicated antibodies.

DETAILED DESCRIPTION OF THE INVENTION

Figure 2B:
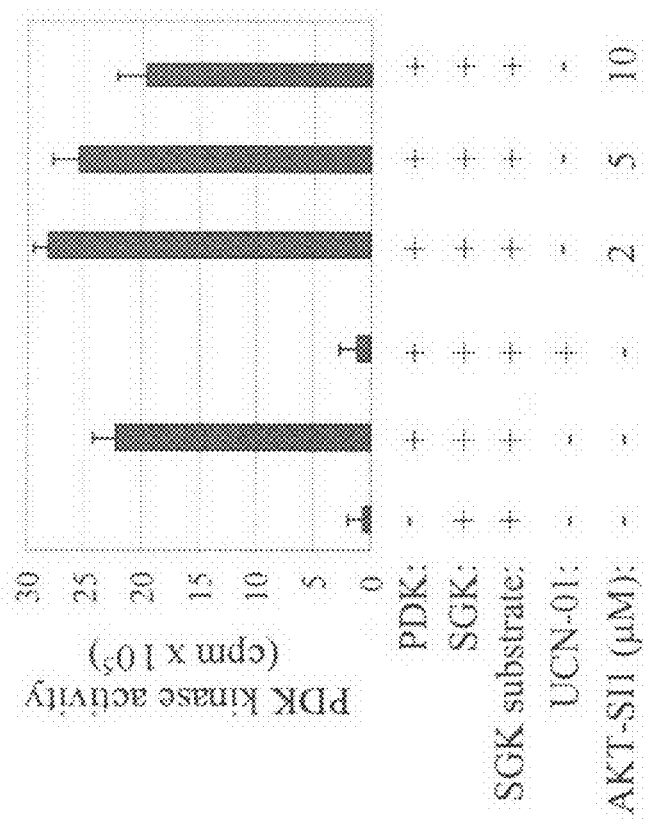

The subject invention concerns compounds and compositions that inhibit the Akt/PKB pathway. In one embodiment, a compound of the invention inhibits kinase activity and/or phosphorylation levels of Akt proteins. Compounds of the invention have the general structure shown in formula I:

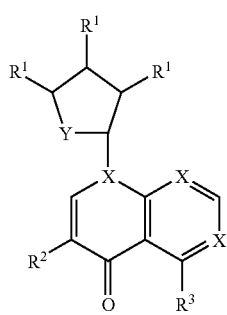

(I)

wherein
X is, independently, O, N, or S;
Y is O, N, or S;
$R^1$ is, independently, —H, —OH, —NH$_2$, —NO$_2$, halogen, alkyl optionally substituted with —OH, or alkoxy optionally substituted with —OH; and,
$R^2$ is —H, —OH, —NH$_2$, —C(O)NH$_2$, alkyl, or alkoxy, any of which can be optionally substituted with —OH, halogen, alkyl, or alkoxy;
$R^3$ is —H, —OH, —NH$_2$, —C(O)NH$_2$, alkyl, or alkoxy, any of which can be optionally substituted with —OH, halogen, alkyl, or alkoxy; or
an analog or a pharmaceutically acceptable salt thereof.

In one embodiment, each X is N. In an exemplified embodiment, Y is O. In another exemplified embodiment, each $R^1$ is independently —OH or —CH$_2$OH—. In still another embodiment, $R^2$ is —NH$_2$ optionally substituted with —OH. In a further embodiment, $R^2$ is —C(O)NH$_2$.

In a specific embodiment, a compound of the invention has the structure (formula II):

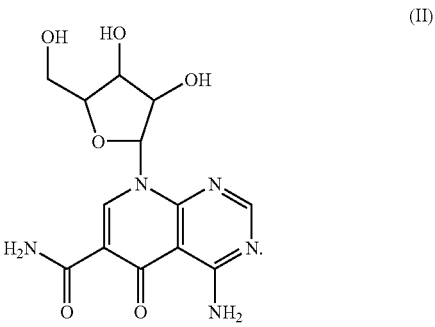

(II)

Compounds of the invention inhibit not only highly activated wild-type Akt resulting from alterations of upstream regulators such as PTEN mutation but also constitutively active Akt mutants including myr-AKT1, Myr-AKT2 and E40K-AKT1. A recent study identified a recurring somatic mutation in PH domain of AKT1 in human breast, colorectal and ovarian cancers that results in a glutamic acid to lysine substitution at amino acid 17 (E17K) in the lipid-binding pocket (Carpten et al. 2007). Lys 17 alters the electrostatic interactions of the pocket and forms new hydrogen bonds with a phosphoinositide ligand. This mutation activates AKT1 through pathological localization to the plasma membrane, transforms cells and induces leukaemia in mice. Further, the E17K substitution reduces the sensitivity to an allosteric kinase inhibitor (Carpten et al. 2007). As E40K-AKT1 mutant is similar to E17K which can localize in the plasma membrane (Bellacosa et al. 1998), API-1 may also inhibit E17K-AKT1.

While compounds of the invention can be administered as isolated compounds, these compounds can also be administered as part of a pharmaceutical composition. The subject invention thus further provides compositions in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The compounds of the invention can be formulated according to known methods for preparing pharmaceutically useful compositions. Formulations are described in a number of sources which are well known and readily available to those skilled in the art. For example, *Remington's Pharmaceutical Science* (Martin 1995) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

As used herein, alkyl means straight or branched chain, saturated or mono- or polyunsaturated hydrocarbon groups having from 1 to 20 carbon atoms and $C_{1-X}$ alkyl means straight or branched chain alkyl groups containing from one up to "X" number of carbon atoms. For example, $C_{1-6}$ alkyl means straight or branched chain alkyl groups containing from one up to 6 carbon atoms. Alkoxy means an alkyl-O-group in which the alkyl group is as previously described herein.

The term "halogen" means a halogen of the periodic table, such as fluorine, chlorine, bromine, or iodine.

The term "optionally substituted" means optionally substituted with one or more of the organic or inorganic groups (e.g., alkyl, aryl, heteroaryl, acyl, alkenyl, cycloalkyl, heterocycloalkyl, cycloalkenyl, heterocycloalkenyl, or halogen), at any available position or positions.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Specifically, "alkyl" can include, for example, methyl, ethyl, propyl, isopropyl, butyl, iso-butyl, sec-butyl, pentyl, 3-pentyl, hexyl, heptyl, octyl, nonyl, decyl, undecyl, dodecyl, tridecyl, tetradecyl, pentadecyl, vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradecenyl, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, or 14-pentadecenyl; "alkoxy" can include methoxy, ethoxy, propoxy, isopropoxy, butoxy, iso-butoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy.

The compounds of the present invention include all hydrates and salts that can be prepared by those of skill in the art. Under conditions where the compounds of the present invention are sufficiently basic or acidic to form stable non-toxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of a compound may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

As used herein, the term "analogs" refers to compounds which are substantially the same as another compound but which may have been modified by, for example, adding side groups, oxidation or reduction of the parent structure. Analogs of compounds of the invention can be readily prepared using commonly known standard reactions. These standard reactions include, but are not limited to, hydrogenation, alkylation, acetylation, and acidification reactions. Chemical modifications can be accomplished by those skilled in the art by protecting all functional groups present in the molecule and deprotecting them after carrying out the desired reactions using standard procedures known in the scientific literature (Greene et al. 1999; Honda et al. 1997; Honda et al. 1998; Konoike et al. 1997; Honda et al. 2000; each of which are hereby incorporated herein by reference in their entirety). Analogs exhibiting the desired biological activity (such as induction of apoptosis, cytotoxicity, cytostaticity, induction of cell cycle arrest, anti-angiogenic properties, etc.) can be identified or confirmed using cellular assays or other in vitro or in vivo assays.

It will be appreciated that compounds of the invention can contain one or more asymmetrically substituted carbon atoms (i.e., carbon centers). The presence of one or more of the asymmetric centers in a compound of the invention, can give rise to stereoisomers, and in each case, the invention is to be understood to extend to all such stereoisomers, including enantiomers and diastereomers, and mixtures including racemic mixtures thereof.

Compounds and compositions of the invention are useful for various non-therapeutic and therapeutic purposes. The compounds and compositions may be used for reducing aberrant cell growth in animals and humans. Because of Such anti-proliferative properties of the compounds, they are useful in reducing unwanted cell growth in a wide variety of settlings including in vitro and in vivo.

Therapeutic application of compounds and compositions containing them can be accomplished by any suitable therapeutic method and technique presently or prospectively known to those skilled in the art. Further, compounds of the invention have use as starting materials or intermediates for the preparation of other useful compounds and compositions.

Compounds of the invention, and compositions thereof, may be locally administered at one or more anatomical sites, such as sites of unwanted cell growth (such as a tumor site or benign skin growth, e.g., injected or topically applied to the tumor or skin growth) or sites of fungal infection, optionally in combination with a pharmaceutically acceptable carrier such as an inert diluent. Compounds of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Compounds and compositions of the invention, including pharmaceutically acceptable salts or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds of the invention may be applied in as a liquid or solid. However, it will generally be desirable to administer them topically to the skin as compositions, in combination with a dermatologically acceptable carrier, which may be a solid or a liquid. Compounds and compositions of the subject invention can be applied topically to a subject's skin to reduce the size (and may include complete removal) of malignant or benign growths, or to treat an infection site. Compounds of the invention can be applied directly to the growth or infection site. Preferably, the compounds are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. No. 4,608,392; U.S. Pat. No. 4,992,478; U.S. Pat. No. 4,559,157; and U.S. Pat. No. 4,820,508.

Useful dosages of the compounds and pharmaceutical compositions of the present invention can be determined by comparing their in vitro activity, and in vivo activity in animal models. Methods for the extrapolation of effective dosages in nice, and other animals, to humans are known to the art; for example, see U.S. Pat. No. 4,938,949.

The present invention also concerns pharmaceutical compositions comprising a compound Of the invention in combination with a pharmaceutically acceptable carrier. Pharmaceutical compositions adapted for oral, topical or parenteral administration, comprising an amount of a compound constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

The subject invention also concerns methods for inhibiting the survival or proliferation or killing a cancer or tumor cell or other cell in which expression of an Akt protein is elevated or constitutively active, comprising contacting the cell with an effective amount of a compound of formula I, or a salt or analog thereof. In a specific embodiment, the compound has the structure shown in formula II, or a salt or analog thereof. In one embodiment, the cell is a human cell or other mammalian cell. Cancer cells that can be inhibited or killed using the subject methods include those cells that are metastatic in nature. Thus, inhibition of metastasis of a cancer or tumor cell is also contemplated by the present invention. The methods can be practiced in vitro or in vivo.

The subject invention also concerns methods for treating oncological disorders, such as cancer or a tumor in a person or animal comprising administering an effective amount of a compound of formula I, or a salt or analog thereof, to the person or animal. In a specific embodiment, a compound has the formula shown in formula II, or a salt or analog thereof. In one embodiment, an effective amount of a compound or composition of the present invention is administered to a patient having an oncological disorder and who is in need of treatment thereof. The inhibitor can be administered prior to, subsequent to, or in conjunction with chemotherapy, immunotherapy and/or radiotherapy. Methods of the invention can optionally include identifying a patient who is or may be in need of treatment of an oncological disorder. Patients in need of treatment using the methods of the present invention can be identified using standard techniques known to those in the medical or veterinary professions, as appropriate. In one embodiment, the patient can be a human or other mammal, such as a primate (monkey, chimpanzee, ape, etc.), dog, cat, cow, pig, or horse, or other animals having an oncological disorder. Means for administering and formulating compounds of the invention for administration to a patient are known in the art, examples of which are described herein. Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include carcinomas, Karposi's sarcoma, melanoma, mesothelioma soft tissue sarcoma, leukemia (acute lymphoblastic, acute myeloid, chronic lymphocytic, chronic myeloid, and other), and lymphoma (Hodgkin's and non-Hodgkin's), and multiple myeloma.

For the treatment of oncological disorders, compounds and compositions contemplated by the present invention can be administered to a patient in need of treatment prior to, subsequent to, or in combination with other antitumor or anticancer agents or substances (e.g., chemotherapeutic agents, immunotherapeutic agents, radiotherapeutic agents, etc.) and/or with radiation therapy and/or with surgical treatment to remove a tumor. For example, compounds and compositions of the present invention can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, anti-angiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genetech, Inc.), respectively. These other substances or radiation treatments may be given at the same as or at different times from the compounds of this invention. Examples of other chemotherapeutic agents contemplated within the scope of the invention include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of immunotherapeutic agents contemplated within the scope of the invention include, but are not limited to, alemtuzumab, cetuximab (ERBITUX), gemtuzumab, iodine 131 tositumomab, rituximab, trastuzamab (HERCEPTIN). The subject invention also concerns methods for treating an oncological disorder comprising administering an effective amount of a compound of the invention prior to, subsequent to, and/or in combination with administration of a chemotherapeutic agent, an immunotherapeutic agent, a radiotherapeutic agent, or radiotherapy.

The subject invention also concerns methods for inhibiting the Akt/PKB pathway in a cell by contacting the cell with an effective amount of a compound or composition of the invention. In one embodiment, the compound binds to and inhibits the activity of an Akt1, AKT2, and/or AKT3 protein. In a specific embodiment, the compound has the structure shown in formula II, or a salt or analog thereof. In one embodiment, the cell is a human or mammalian cell, and can be a cancer or tumor cell or other cell that exhibits abnormal proliferation, survival, migration or differentiation. In one embodiment, the cell constitutively expresses or expresses elevated or abnormal levels of an Akt protein, such as Akt1, AKT2, and/or AKT3.

The subject invention also concerns methods for treating a person or animal having a disorder associated with constitutive, abnormal, or elevated expression of an Akt protein in a cell, wherein a therapeutically effective amount of a compound or composition of the invention is administered to the person or animal. The disorder can be one characterized, for example, by abnormal cell proliferation, cell survival, cell migration, and/or cell differentiation. In one embodiment, the compound binds to and inhibits activity of an Akt1, AKT2, and/or AKT3 protein. In a specific embodiment, the compound has the structure shown in formula II, or a salt or analog thereof Depending upon the disorder or disease condition to be treated, a suitable dose(s) may be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The subject invention also concerns kits comprising one or more compounds of the invention, or a composition comprising a compound of the invention, or an analog or salt of the foregoing, in one or more containers. In one embodiment, the kit comprises a compound of formula II, or a pharmaceutically acceptable salt or analog thereof. Kits of the invention can optionally include pharmaceutically acceptable carriers and/or diluents. In one embodiment, a kit of the invention includes one or more other components, adjuncts, or adjuvants as described herein. In another embodiment, a kit includes one or more anti-cancer agents, such as those agents described herein. In one embodiment, a kit of the invention includes instructions or packaging materials that describe how to administer a compound or composition of the kit. Containers of the kit can be of any suitable material, e.g., glass, plastic, metal, etc., and of any suitable size, shape, or configuration. In one embodiment, a compound of the invention is provided in the kit as a solid, such as a tablet, pill, or powder form. In another embodiment, a compound of the invention is provided in the kit as a liquid or solution. In one embodiment, the kit comprises an ampoule or syringe containing a compound of the invention in liquid or solution form.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cells of such human and non-human species.

Materials and Methods

Cell Lines and NCI Diversity Set. All cell lines used in this study were either purchased from ATCC or described previously (Cheng et al. 1997; Jiang et al. 2000; Yang et al. 2004; Yang et al. 2005). The NCI Structural Diversity Set is a library of 1,992 compounds selected from the approximately 140,000-compound NCI drug depository. In-depth data on the selection, structures, and activities of these diversity set compounds can be found on the NCI Developmental Therapeutics Program web site (Jones et al. 1991).

Screening for Inhibition of Akt-transformed Cell Growth. AKT2 transformed NIH3T3 cells or LXSN vector-transfected NIH3T3 control cells (Cheng et al. 1997) were plated into 96-well tissue culture plate. Following treatment with 5 µM of NCI Diversity Set compound, cell growth was detected with CellTier 96 One Solution Cell Proliferation kit (Promega). Compounds that inhibit growth in AKT2-transformed but not LXSN-transfected NIH3T3 cells were considered as candidates of Akt inhibitor and subjected to further analysis.

In vitro Protein Kinase, Cell Survival and Apoptosis Assays. In vitro kinase was performed as previously described (Jiang et al. 2000). Cell survival was assayed with MTT (Sigma). Apoptosis was detected with annexin V (BD Biosciences), which was performed according to manufacture's instruction. Recombinant Akt and PDK1 were purchased from Upstate Biotechnology Inc.

Antitumor Activity in the Nude Mouse Tumor Xenograft Model. Tumor cells were harvested, resuspended in PBS, and injected subcutaneous (s.c.) into the right and left flanks ($2 \times 10^6$ cells/flank) of 8-week-old female nude mice as reported previously (Sun et al. 1999). When tumors reached about 100-150 $mm^3$, animals were randomized and dosed intraperitoneal (i.p.) with vehicle or drug daily. Control animals received dimethylsulfoxide (DMSO) (20%) vehicle and treated animals were injected with API-1 (10 mg/kg/day) in 20% DMSO.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Identification of Small Molecule Akt/PKB Pathway Inhibitor-1, API-1, by Screening NCI Diversity Set Due to the fact that aberrant activation of Akt pathway occurs in almost 50% all the human malignancy and inhibition of Akt induces cell growth arrest and apoptosis, it has drawn interest from industry and academia to develop small molecule Akt inhibitor for anti-cancer drug discovery (Cheng et al. 2005; Granville et al. 2006). While a dozen Akt inhibitors have been reported, many of them lack anti-tumor activity in vivo. A lipid-based Akt inhibitor, perifosine, has been reported in phase I and II studies (Van Ummersen et al. 2004; Bailey et al. 2006). However, in neither study was modulation of Akt assessed. A recent phase II study of perifosine in pancreatic cancer was terminated as a result of unacceptable adverse events during the first stage (Marsh et al. 2007). Nevertheless, there is a need to develop potent selective Akt inhibitors that are void of inhibiting other kinase activities with minimal adverse effect. To identify small molecule inhibitor(s) of Akt, we have evaluated a chemical library of 1,992-compounds from the NCI (the NCI Diversity Set) for agents capable of inhibition of growth in AKT2-transformed but not empty vector LXSN-transfected NIH3T3 cells as described in "Materials and Methods". Triple experiments showed that 32 compounds inhibited growth only in AKT2-transformed cells. We previously characterized one of them, named API-2/triciribine that is a pan-Akt inhibitor with antitumor activity in vitro and in vivo and currently in phase I clinic trail (Yang et al. 2004).

In the present study, we showed that Akt/PKB inhibitor-1 (API-1) specifically inhibits kinase activity and phosphorylation levels of Akt in living cells. FIG. 1A shows the chemical structure of API-1 (NSC 177223), which has no chemical name and has not been tested in NCI 60 cell lines (http://dtp.nci.nih.gov/). Since APT-1 inhibited selectively AKT2 transformed cells over untransformed parental cells, we first examined whether API-1 is an inhibitor of AKT2 kinase and whether it also inhibits other two members of Akt. HEK293 cells were transfected with HA-tagged wild type Akt1, AKT2 and AKT3. Following serum starvation for overnight, cells were treated with APT-1 for 60 min prior to EGF stimulation and immunoprecipitated with anti-HA antibody. The immunoprecipitates were subjected to in vitro kinase assay. FIG. 1B shows that API-1 suppressed insulin-induced kinase activity of Akt1, AKT2 and AKT3. We next examine if API-1 inhibits Akt in living calls. OVCAR3 cells, which express elevated levels of phosphor-Akt, were treated with different doses of API-1 for 3 hours. Immunoblotting analysis with anti-phospho-Akt-S473 antibody showed that API-1 efficiently reduced phosphorylation level of Akt and $IC_{50}$ is approximately at 0.8 µM. However, total Akt levels were no change (FIG. 1C). Further, we examined if API-1 directly inhibits Akt kinase activity in vitro. Recombinant constitutively active Akt protein was incubated with Akt/SGK substrate peptide (Upstate) in a kinase buffer containing different amounts of API-1 and compound E, a pan-kinase ATP-competitor inhibitor including Akt, as positive control. Triple experiments showed no effect of APT-1 on Akt kinase activity (FIG. 1D), suggesting that API-1 does not directly inhibit Akt in vitro and that API-1 functions neither as ATP nor substrate competitor.

Example 2

APT-1 does not Inhibit Upstream Activators of Akt

Figure 2A:
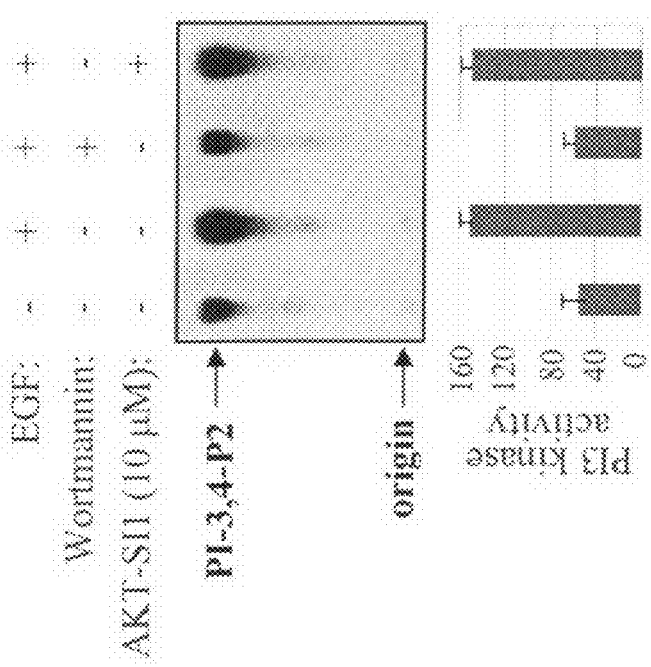
Figure 2C:
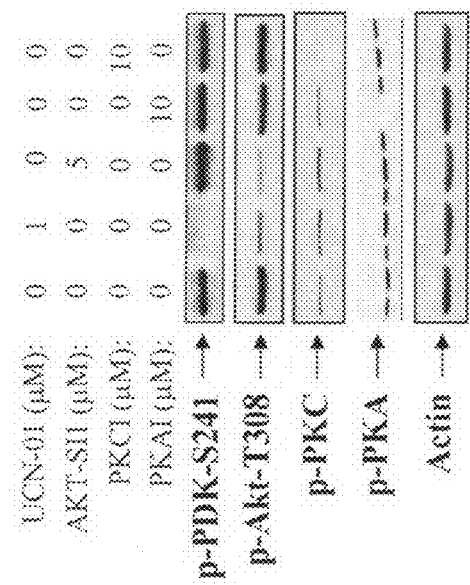
Figure 2D:
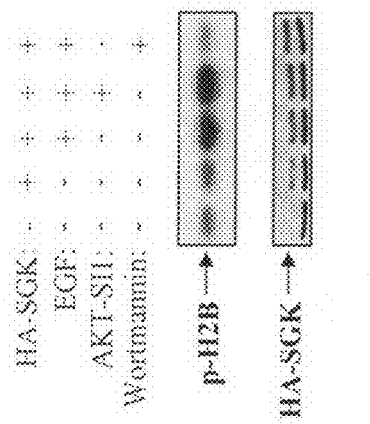

Akt is activated by extracellular stimuli and intracellular signal molecules through a PI3K-dependent manner, which is negatively regulated by PTEN. Activation of PI3K or mutation of PTEN will activate PDK1 leading to induction of Akt kinase activity. Therefore, APT-1 inhibition of Akt could result from targeting upstream molecule(s) of Akt, such as PI3K and PDK1. To this end, we next examined if APT-1 inhibits PI3K and/or PDK1. HEK293 cells were serum-starved and then treated with API-1 or PI3K inhibitor, wortmannin, for 1 hour prior to EGF stimulation. PI3K was immunoprecipitated with anti-p110α antibody. The immunoprecipitates were subjected to in vitro PI3K kinase assay using PI-4-P as a substrate. As shown in FIG. 2A, the EGF-induced PI3K activity was inhibited by wortmannin but not by APT-1. To evaluate the effect of APT-1 on PDK1, we performed in vitro PDK1 kinase assay using SGK kinase as readout (Upstate Biotechnology Inc.). Unlike PDK1 inhibitor UCN-01 (Sato et al. 2002), API-1 had no effect on in vitro PDK1 kinase activity (FIG. 2B). To further evaluate the effect of API-1 on PDK1 activation in living cells, we examined phosphorylation level of PDK1-Ser241, a residue that is autophosphorylated and is critical for its activity (Casamayor et al. 1999), following API-1 treatment of OVCAR3 cells. FIG. 2D shows that phosphorylation levels of PDK1 were not inhibited by API-1.

Example 3

API-1 is Highly Selective for the Akt Over AGC Kinase Members PKA, PKC and SGK, and Other Signaling Molecules ERK, JNK, p38, and STAT3

Figure 2E:
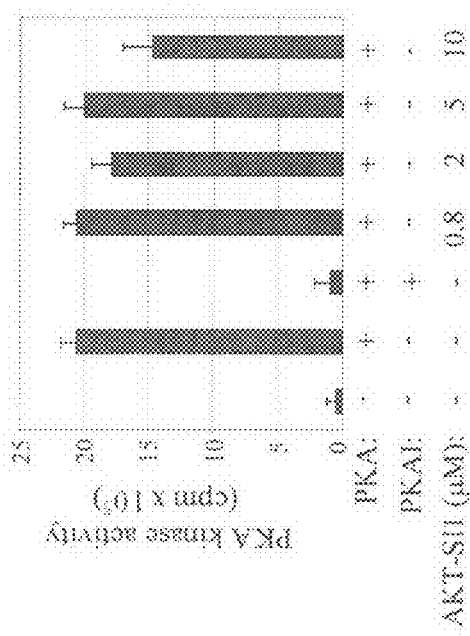
Figure 2F:
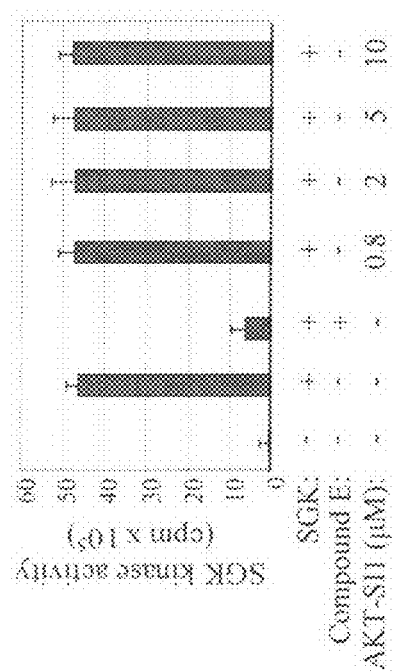

Akt belongs to AGC (PKA/PKG/PKC) kinase family, which also include PKA, PKC, serum- and glucocorticoid-inducible kinase (SGK), p90 ribosomal S6 kinase, $p70^{S6K}$, mitogen- and stress-activated protein kinase and PKC-related kinase. Among AGC kinase family, protein structures of PKA, PKC and SGK are much closer to Akt kinase than other members. Therefore, we next examined the effects of API-1 on the enzymatic activities of these 3 kinases. In vitro PKA kinase assay and SGK kinase assay was performed by pre-incubated indicated dose of API-1 or specific inhibitor with recombinant PKA or SGK protein for 30 minutes before starting kinase assay by adding kemptide or Akt/SGK substrate peptide and [γ-$^{32}$] ATP in kinase buffer. In vitro kinase assay showed that the kinase activities of PKA and SGK were inhibited by PKAI and compound E respectively, whereas API-1 exhibited no effect on their activities (FIGS. 2C and 2E). To further evaluate the effect of API-1 on the PKA and PKCα activation in living cells, OVCAR3 cells were treated with indicated doses of API-1 or specific inhibitor of PKA and PKC, immunoblotting analysis showed that phosphorylation levels of PKA and PKC were not inhibited by API-1 (FIG. 2D). In addition, HEK293 cells were transfected with HA-tagged SGK. In vitro kinase assay showed that EGF-induced SGK kinase activity was attenuated by wortmannin but not API-1 (FIG. 2F).

To determine whether API-1 has effect on other oncogenic survival pathways, OVCAR3 cells were treated with API-1 (10 αM) for different times and immunoblotted with commercially available anti-phospho-antibodies. We did not observe the detectable changes of phosphorylation levels of Stat3, JNK, p38 and Erk1/2 after API-1 treatment (FIG. 2G). These data indicate that API-1 could specifically inhibit the Akt pathway.

Example 4

API-1 Inhibits Constitutively Active Akt and its Downstream Targets

Since API-1 could not directly inhibit Akt in vitro but abrogated kinase activity and phosphorylation of Akt in the living cells without effect on PI3K and PDK1, this led us to assume that this compound may interact with Akt protein, but not ATP-binding site, to prevent it from phophorylation of Thr308 and Ser473 by PDK1 and PDK2. If this is authentic, API-1 should also inhibit activation of constitutively active Akt since its activation still requires phosphorylation of Thr308 and Ser473 (Sun et al. 2001). To test this hypothesis, HEK293 cells were transfected with HA-tagged Myr-Akt1-Akt2 and -Akt1E40K. Following serum starvation overnight, cells were treated with or without API-1. Myr-Akt1, Myr-Akt2 and Akt1-E40K were immunoprecipitated with anti-HA antibody. The immunoprecipitates were subjected to in vitro kinase assay and immunoblotting analysis with anti-phospho-Akt-T308 antibody. FIG. 3A shows that in vitro Akt kinase activity as well as phosphorylation levels of Myr-Akt1, Myr-Akt2 and Akt1-E40K were inhibited by API-1, supporting the notion that API-1 might bind to Akt molecule to prevent it from activation within the cells.

Figures 3B, 3C, 3D:
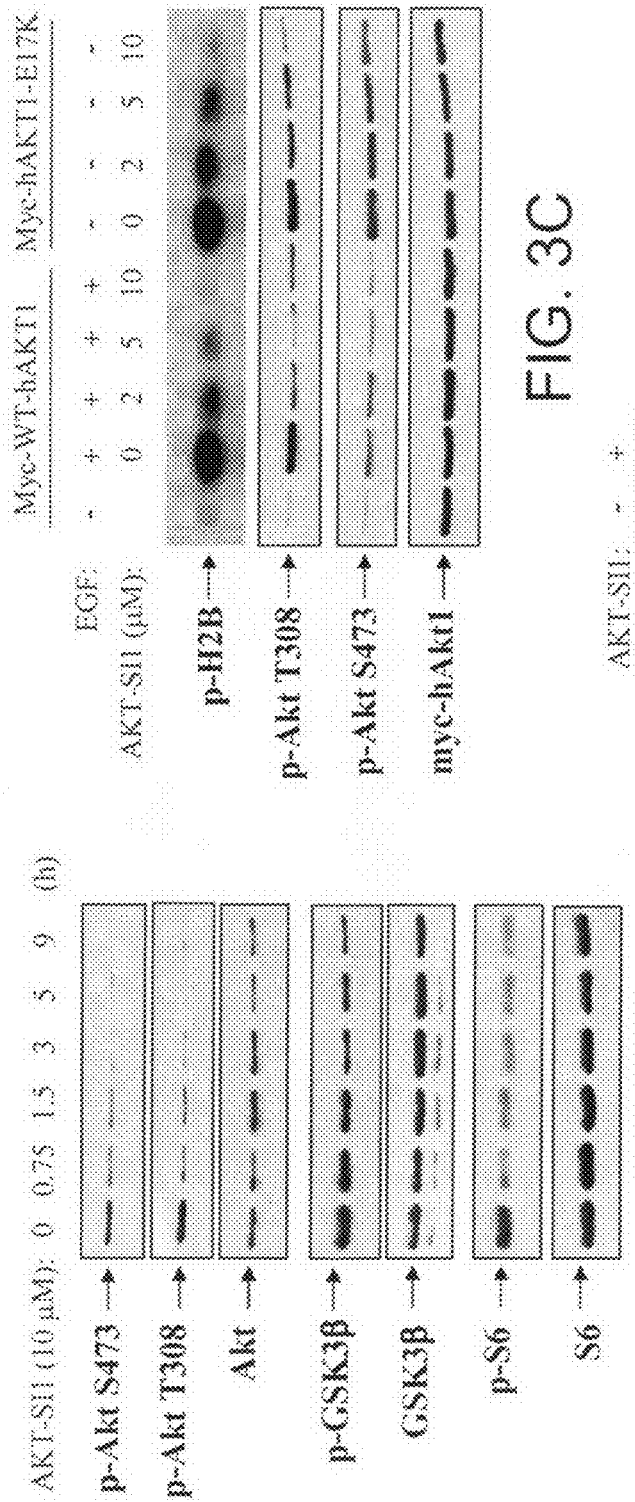

Akt exerts its cellular function through phosphorylation of a number of proteins (Datta et al. 1999). We next examined whether API-1 inhibits downstream targets of Akt. Since GSK3β and mTOR are two of the major Akt targets, we evaluated the effects of API-1 on phosphorylation levels of GSKβ and S6, a substrate of $p70^{S6K}$. Following treatment of OVCAR3 with API-1, immunoblotting analysis revealed that API-1 largely inhibited their phosphorylation (FIG. 3B).

Example 5

Figure 4A:
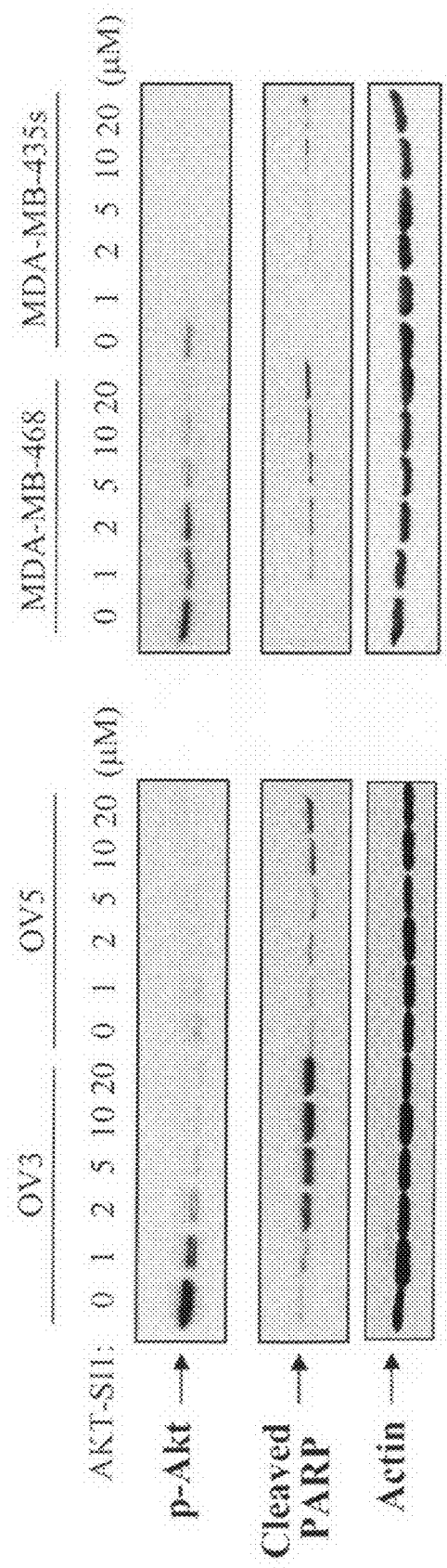
FIGS. 4A-4G are graphs showing that API-1 inhibits Akt activity and cell growth and induces apoptosis in human cancer cells with elevated Akt.
Figure 4C:
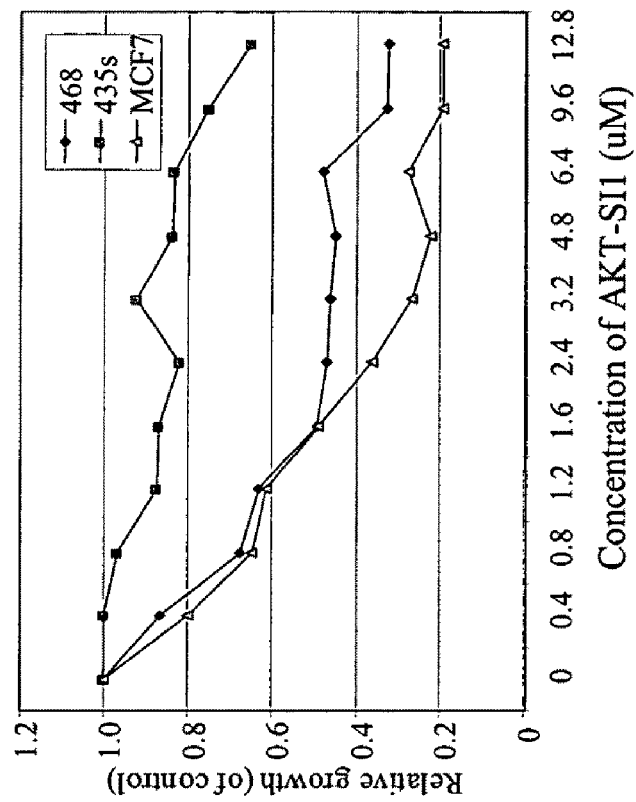
Figure 4B:
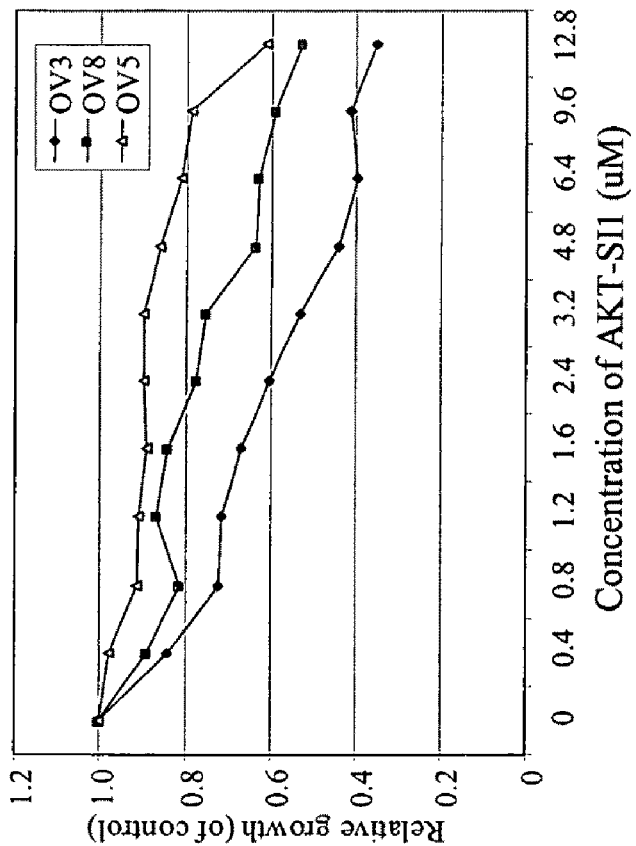
Figures 4D, 4E:
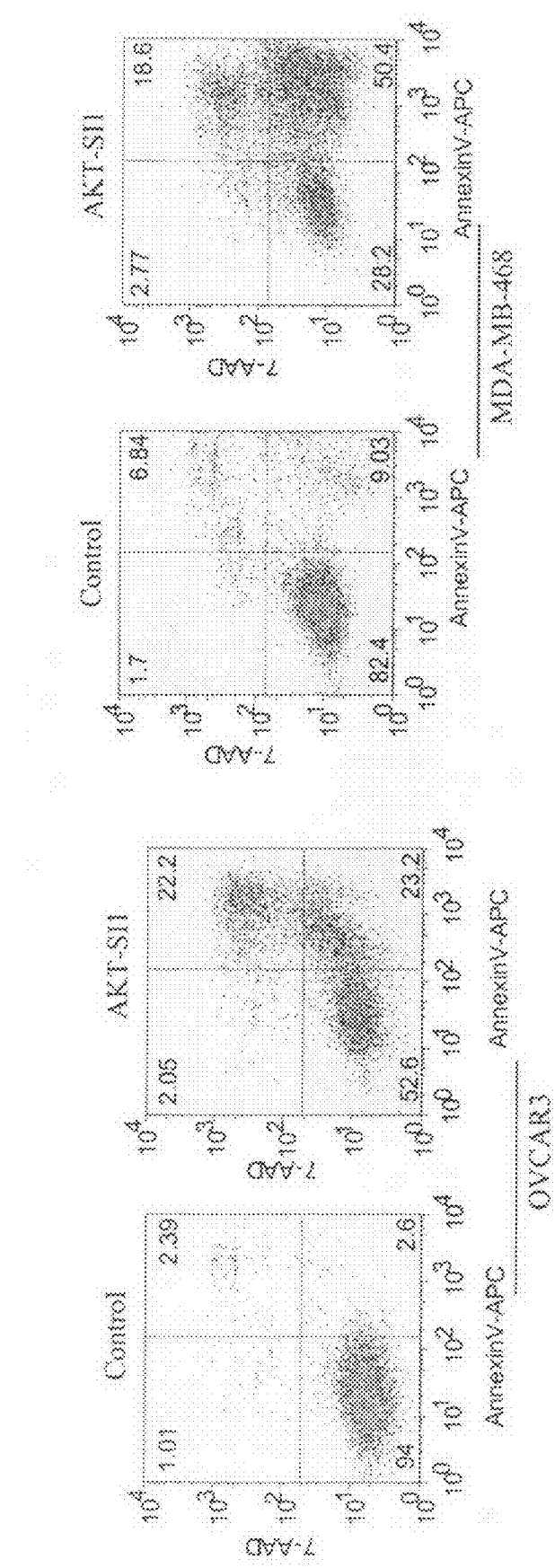
Figures 4F, 4G:
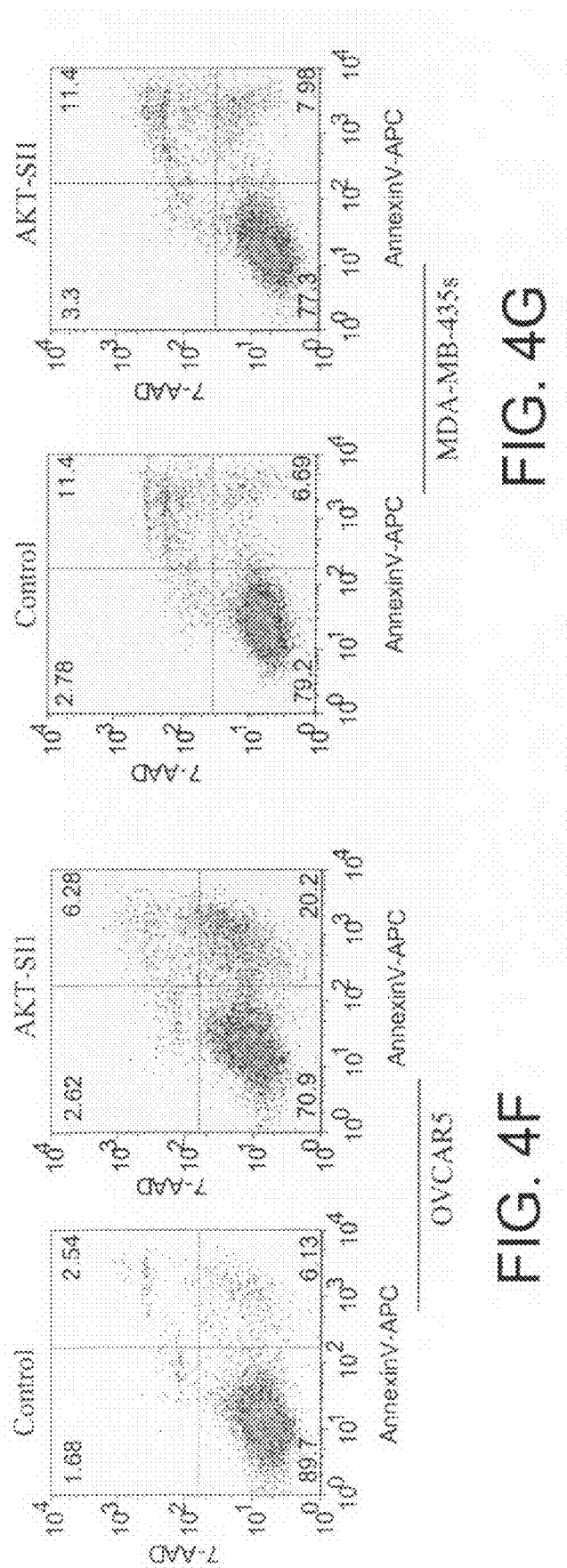

API-1 Suppresses Cell Growth and Induces Apoptosis in Akt-Overexpressing/Activating Human Cancer Cell Lines Akt is a major pro-growth and pro-survival pathway. Cancer cells with elevated Akt kinase exhibit more resistant to chemotherapeutic drug-induced cell growth arrest and cell death whereas knockdown Akt sensitizes to apoptosis induced by different proapoptotic stimuli (Solit et al. 2003; Xu et al. 2003; Jetzt et al. 2003). The ability of API-1 to selectively inhibit the Akt pathway suggests that it should inhibit proliferation and/or induces apoptosis preferentially in those tumor cells with aberrant expression/activation of Akt. To test this, API-1 was used to treat the cells that express constitutively active Akt, caused by overexpression of Akt (OVCAR3, OVCAR8, MCF7 and PANC1) or mutations of the PTEN gene (MDA-MB-468PC-3 and LNCaP), and cells that do not (OVCAR5, MDA-MB-435s, DU-145 and COLO357). Immunoblotting analysis showed that phosphorylation levels of Akt were significantly inhibited by API-1 in the cells expressing elevated Akt while phospho-Akt was also reduced by API-1 in the cell lines exhibiting low levels of Akt (FIG. 4A and data not shown). However, API-1 induces PARP cleavage and inhibits cell growth in a much higher degree in Akt-overexpressing/activating cells as compared to those with low levels of Akt (FIGS. 4A, 4B, and 4C). API-1 treatment inhibited cell proliferation by approximate 50-70% in Akt-overexpressing/activating cell lines, OVCAR3, OVCA8, MDA-MB-468 and MCF7, whereas only by about 10-30% in OVCAR5, and MDA-MB-435s cells (FIGS. 4B and 4C). Moreover, API-1 Induces apoptosis by 9-fold and 4.6-fold in OVACAR3 and MDA-MB-468, respectively, whereas much less apoptosis was observed in API-1-treated OVCAR5 and MDA-MB-435s cells (FIGS. 4D-4G). Thus, API-1 inhibits cell growth and induces apoptosis preferentially in the cells that express aberrant Akt.

Example 6

API-1 Inhibits the Growth of Tumors in Nude Mice that Overexpress Akt

Figures 5A, 5B:
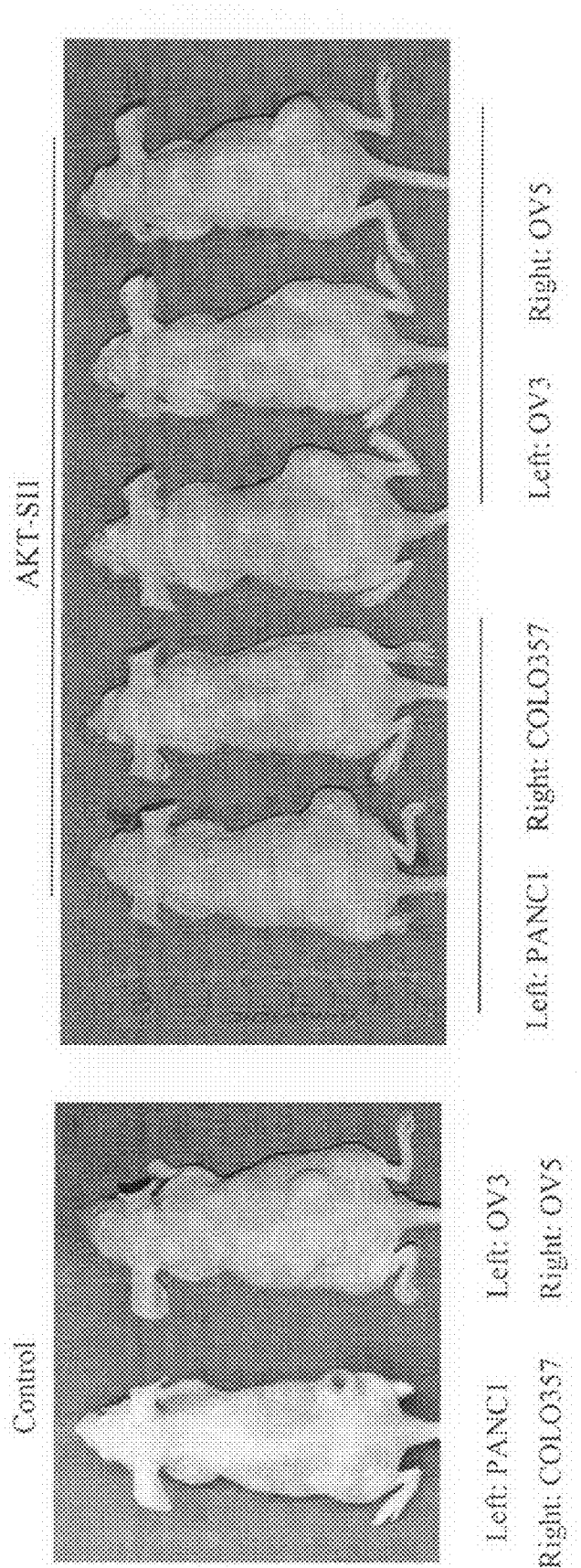
Figure 5D:
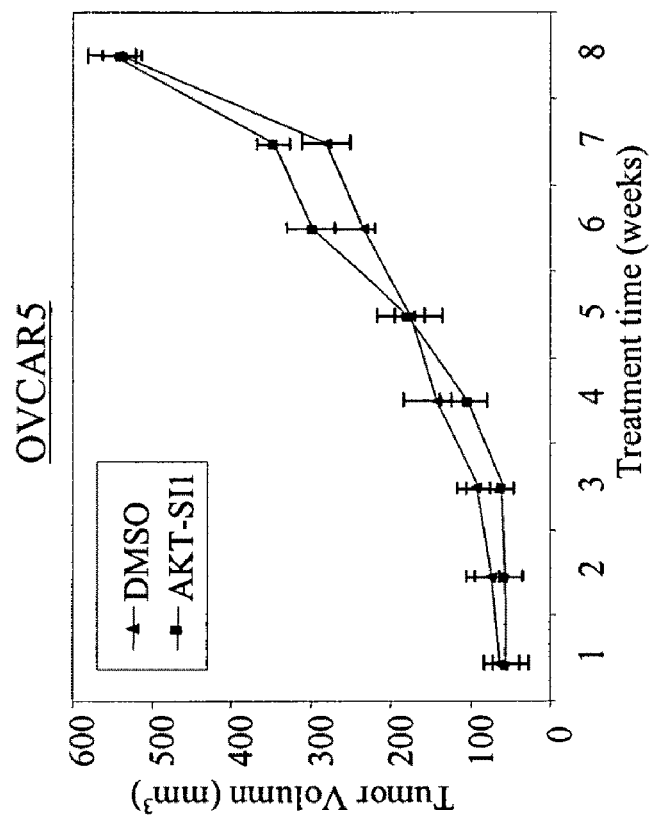
Figure 5C:
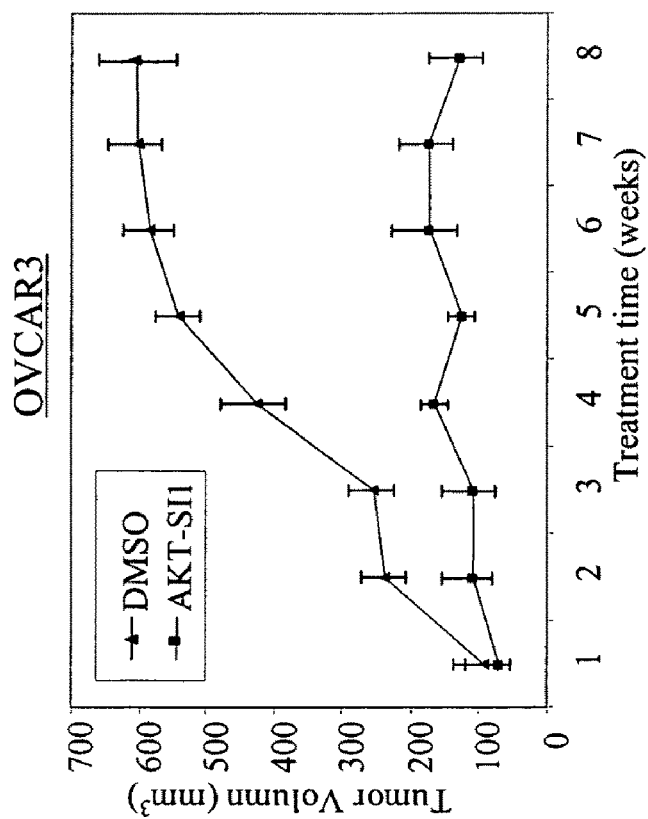
Figure 5F:
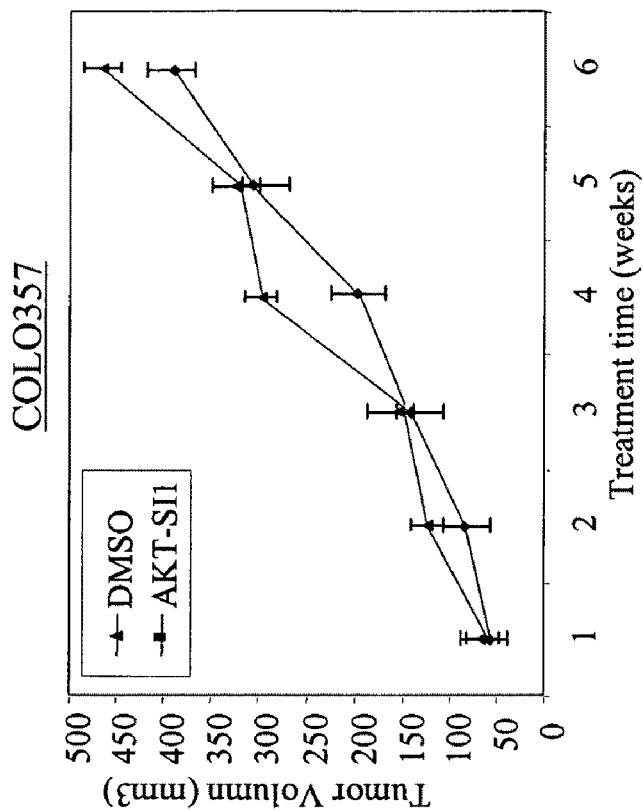
Figure 5E:
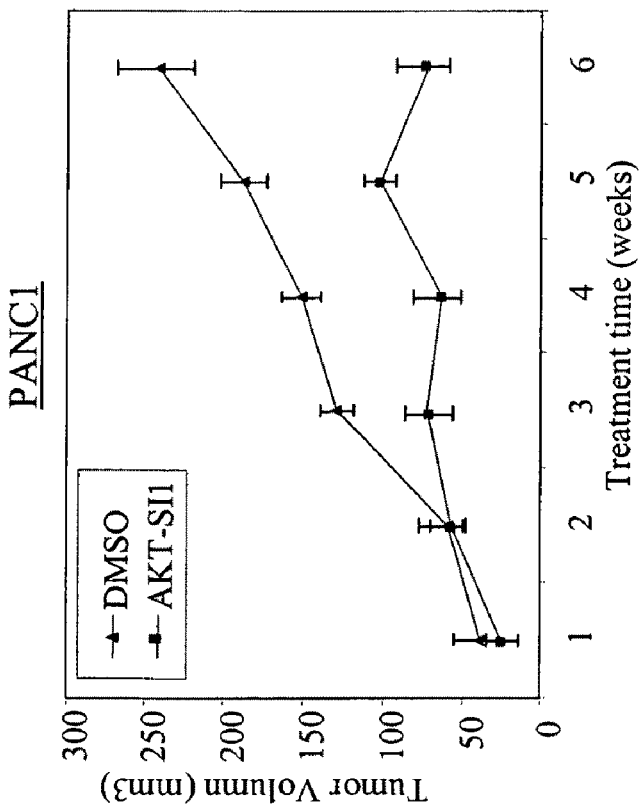
Figures 5G, 5H, 5I, 5J:
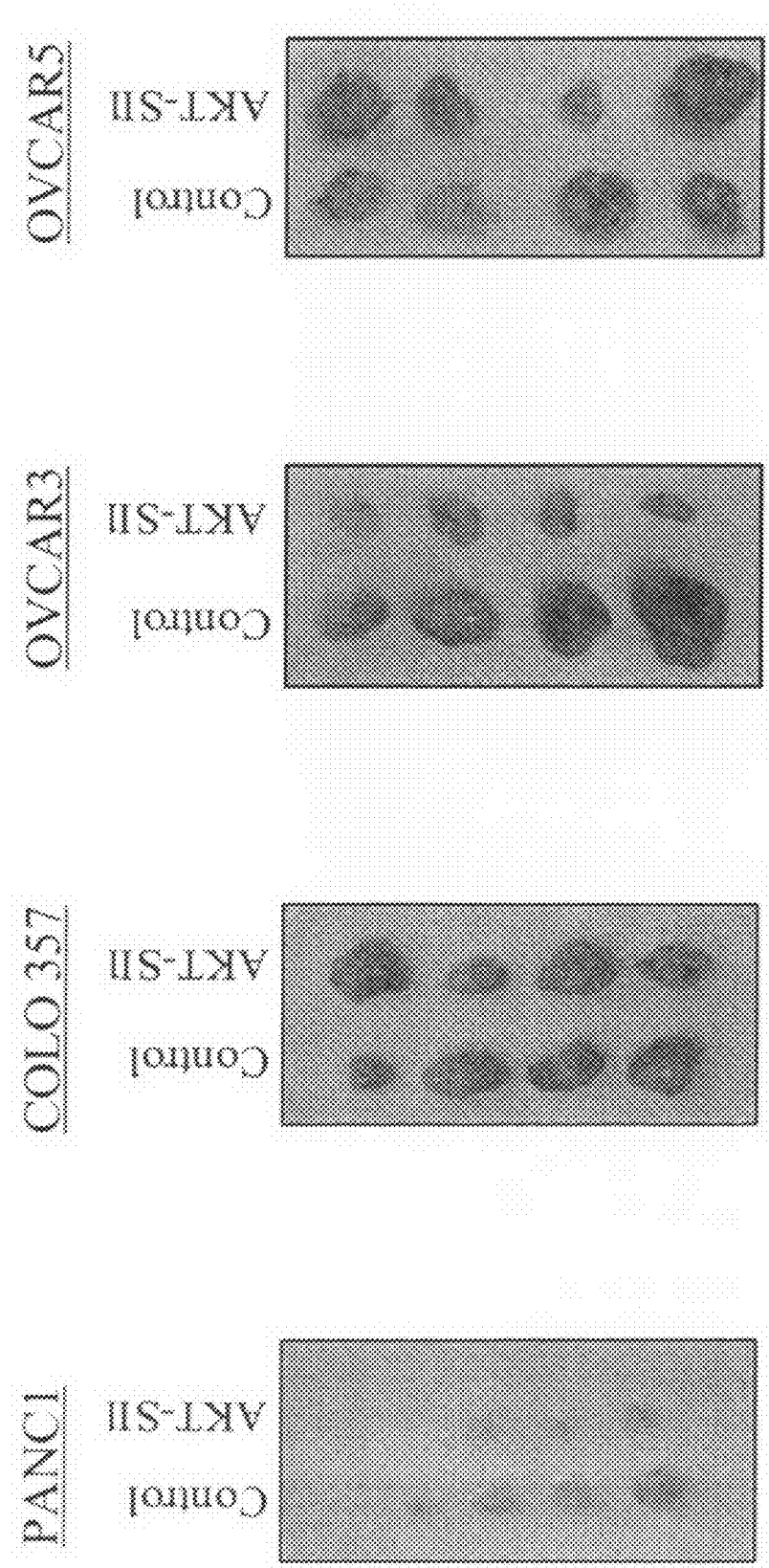
Figures 6A, 6B, 6C:
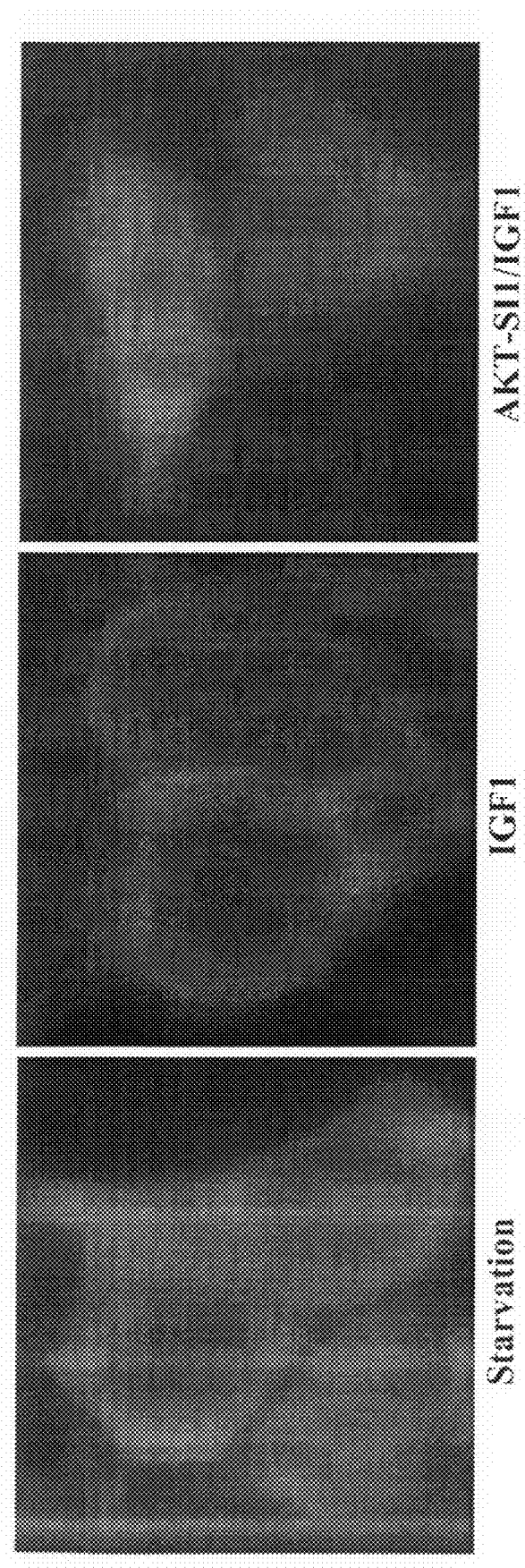
FIGS. 6A-6C show that AKT-SI1 inhibits IGF-1 induced plasma membrane translocation of Akt, HeLa cells were transfected on coverslips with Myc-AKT1, serum-starved overnight and then treated with (FIG. 6C) or without (FIG. 6B) AKT-SI1 for 30 min prior to stimulation with IGF1 for 15 minutes. Following fixation, cells were immuno-stained with the anti-Myc monoclonal antibody, followed by a FITC-conjugated secondary antibody to reveal the presence of the epitope-tagged protein in the cytosol or membrane (FIG. 6B). Cells without treatment with AKT-SI1 and IGF1 were used as control (FIG. 6A).
Figures 7A, 7B, 7C:
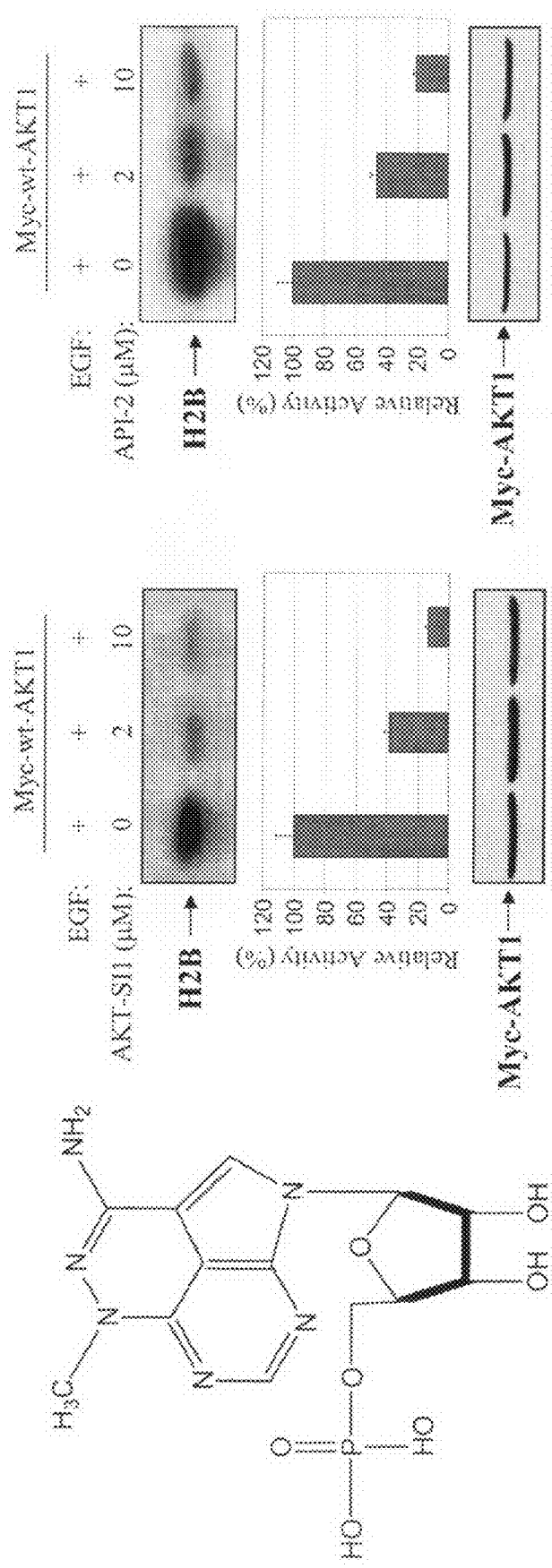
FIGS. 7A-7E show that AKT-SI1 is more potent than API-2/TCN in inhibition of Akt kinase activity, especially constitutively active Akt. While AKT-SI1 structure shares the ribose sugar moeity with API-2/TCN (FIG. 7A), the remaining portion of these 2 molecules have no chemical similarities. Nevertheless, we compared their capability of inhibiting Akt. HEK293 cells were transfected with wild-type Myc-AKT1 (FIGS. 7B and 7C) and constitutively active Myc-AKT1-E17K (FIGS. 7D and 7E). Following 36 h incubation, cells were serum starved overnight. The wild-type Akt-tranfected cells were treated with AKT-SI1 (FIGS. 7B and 7D) or API-2/TCN (FIGS. 7C and 7E) for 30 min and subsequently stimulated with EGF for 15 min. Immunoprecipitation was carried out with anti-Myc antibody and the immunoprecipitates were subjected to in vitro kinase assay using Historic H2B as substrate (top). Inhibition of Akt kinase activity by AKT-SI1 and API-2/TCN was quantified and calculated as relative activity (middle). Western blot analysis shows the immunoprecipitated AKT1 proteins (bottom panels). The experiments were repeated three times.
Figures 7D, 7E:
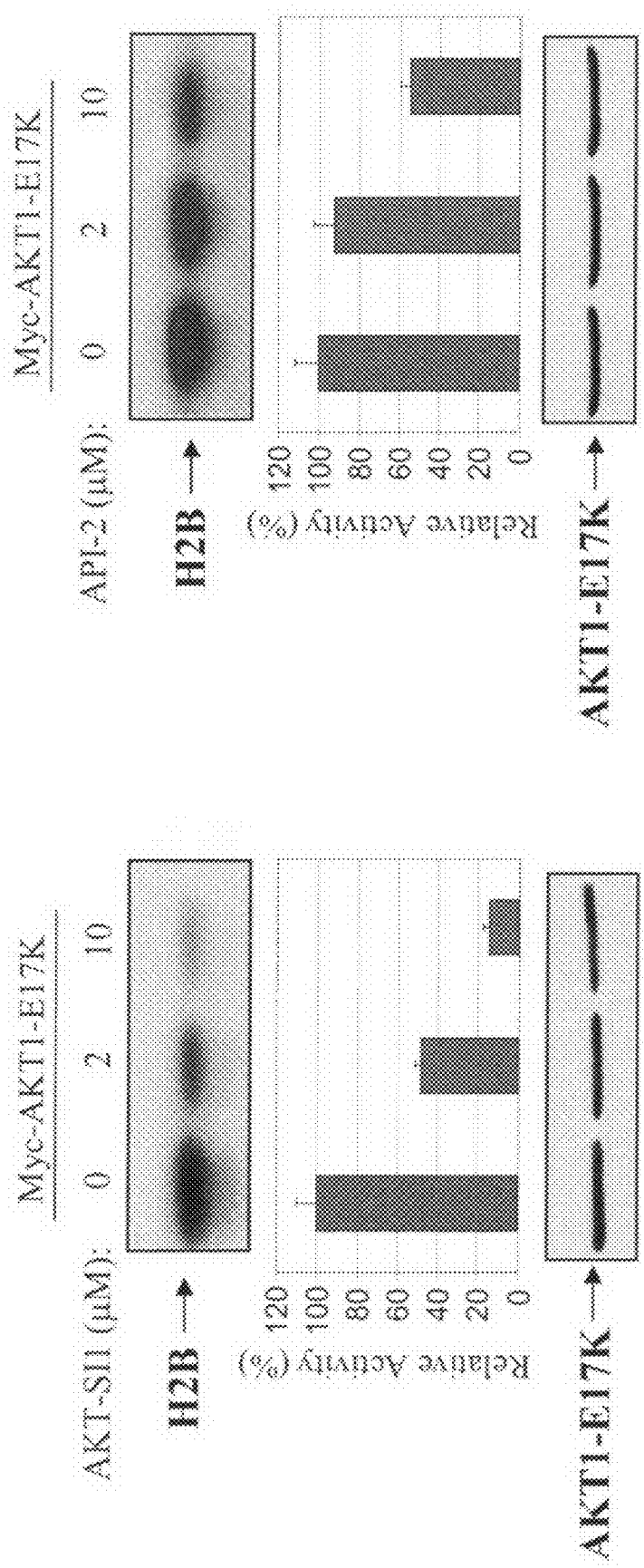
Figures 8A, 8B:
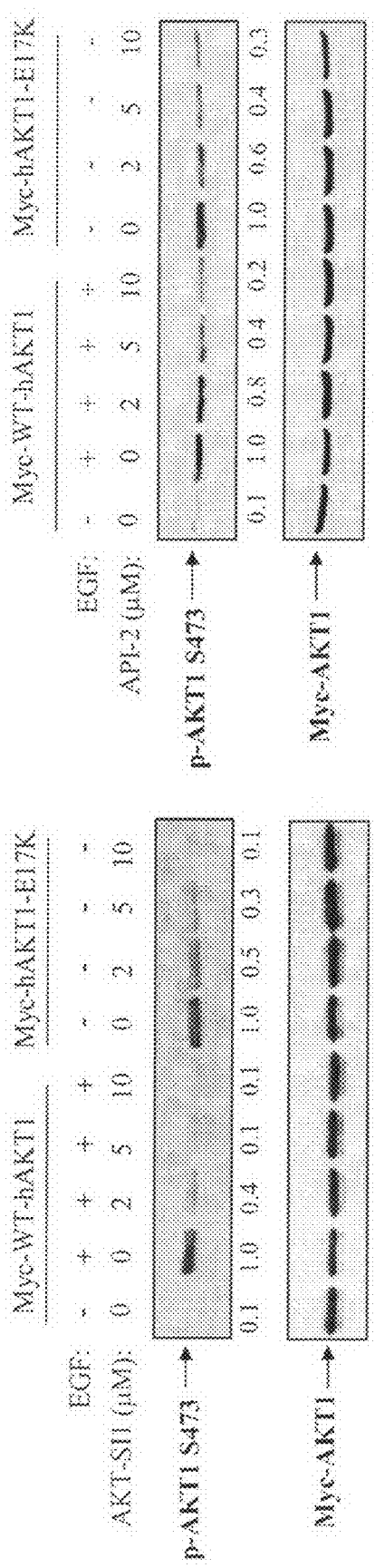
FIGS. 8A and 8B show AKT-SI1 and API-2/TCN inhibit phospho-Akt levels. Wild-type Myc-AKT1 and constitutively active Myc-AKT1-E17K transfected HEK 293 cells were treated with the indicated reagents and immunoblotted with anti-phospho-Akt-S473 (top) and -Myc (bottom) antibodies.

It has previously been shown that aberrant activation and overexpression of Akt are frequently detected in human ovarian and pancreatic cancer (Cheng et al. 1992) and that antisense of Akt significantly inhibits tumor cell growth and invasion (Cheng et al. 1996). Further, inhibition of Akt pathway by inhibitors of PI3K, HSP70, Src and farnesyltransferase resulted in cell growth arrest and induction of apoptosis (Solit et al. 2003; Xu et al. 2003). Because API-1 inhibits Akt signaling and induces apoptosis and cell growth arrest in cancer cells with elevated levels of Akt (FIGS. 4A-4G), it was reasoned that the growth of tumors with elevated levels of Akt should be more sensitive to API-1 than that of tumors with low levels of Akt in nude mice. To this end, Akt-overexpressing cells (OVCAR3 and PANC-1) were s.c. implanted into the left flank, and those cell lines that express low levels of Akt (OVCAR5 and COLO357) were s.c. implanted into the right flank of mice. When the tumors reached an average size of about 100-150 mm$^3$, the animals were randomized and treated i.p. with either vehicle or API-1 (10 mg/kg/day). As illustrated in FIGS. 5A-5J, OVCAR3 and PANC1 tumors treated with vehicle control continued to grow. API-1 inhibited OVCAR3 and PANC1 tumor growth by 70% and 50%, respectively (FIGS. 5C-5F and 5G-5J). In contrast, API-1 had little effect on the growth of OVCAR5 and COLO357 cells in nude mice (FIGS. 5A-5J). At dose 10 mg/kg/day, API-1 had no effects on blood glucose level, body weight, activity and food intake of mice (data not shown). In treated tumor samples, phosphorylation levels of Akt were reduced by API-1 about 70% without change of total Akt content (FIGS. 5K-5L). Taken together, these results indicate that API-1 selectively inhibits the growth of tumors with elevated levels of Akt.

It should be understood that the examples and embodiments described herein are for illustrative purposes only and that various modifications or changes in light thereof will be suggested to persons skilled in the art and are to be included within the spirit aid purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,559,157
U.S. Pat. No. 4,608,392
U.S. Pat. No. 4,820,508
U.S. Pat. No. 4,938,949
U.S. Pat. No. 4,992,478
U.S. Pat. No. 5,167,649
Bailey H H, Mahoney M R, Ettinger D S, et al. (2006) Phase II study of daily oral perifosine in patients with advanced soft tissue sarcoma. Cancer, 107:2462-7.
Bellacosa A, Chan T O, Ahmed N N, et al. (1998) Akt activation by growth factors is a multiple-step process: the role of the PH domain. Oncogene, 17:313-25.
Bellacosa A, Testa J R, Staal S P, Tsichlis P N. (1991) A retroviral oncogene, akt, encoding a serine-threonine kinase containing an SH2-like region. Science, 254: 274-7.
Carpten J D, Faber A L, Horn C, et al. (2007) A transforming mutation ill the pleckstrin homology domain of AKT1 in cancer. Nature; [Epub ahead of print]
Casamayor A, Morrice N A, Alessi D R. (1999) Phosphorylation of Ser-241 is essential for the activity of 3-phosphoinositide-dependent protein kinase-1: identification of five sites of phosphorylation in vivo. Biochemn J, 342:287-92.
Castillo S S, Brognard J. Petukhov P A, et al. (2004) Preferential inhibition of Akt and killing of Akt-dependent cancer cells by rationally designed phosphatidylinositol ether lipid analogues. Cancer Res, 64:2782-92.
Cheng J Q and Nicosia S V. (2001) AKT signal transduction pathway in oncogenesis. In: Schwab D, editor. Encyclopedic Reference of Cancer. Berlin Heidelberg and New York: Springer; p. 35-7.
Cheng J Q, Altomare D A, Klein M A, et al. (1997) Transforming activity and cell cycle-dependent expression of the AKT2 oncogene: evidence for a link between cell cycle regulation and oncogenesis. Oncogene, 14:2793-801.
Cheng J Q, Godwin A K, Bellacosa A, et al. (1992) A putative oncogene encoding a member of a subfamily of protein-serine/threonine kinases, is amplified in human ovarian carcinomas. Proc Natl Acad Sci USA, 89:9267-71.
Cheng J Q, Lindsley C W, Cheng G Z, Yang H, Nicosia S V. (2005) The Akt/PKB pathway: molecular target for cancer drug discovery. Oncogene, 24:7482-92.
Cheng J Q, Ruggeri B, Klein W M, et al. (1996) Amplification of AKT2 in human pancreatic cells and inhibition of AKT2 expression and tumorigenicity by antisense RNA. Proc Natl Acad Sci USA. 93:3636-41.
Datta S R, Brunet A, Greenberg M E. (1999) Cellular survival: a play in three Akts. Genes Dev, 13:2905-27.

Feng J, Park J, Cron P, Hless D, Hemminigs B A. (2004) Identification of a PKB/Akt hydrophobic motif Ser-473 kinase as DNA-dependent protein kinase. J Biol Chem, 279: 41189-96.

Feun L G, Blessing J A, Barrett R T, Hanjani P. (1993) A Phase II trial of tricyclic nucleoside phosphate in patients with advanced squamous cell carcinoma of the cervix: a Gynecologic Oncology Group study. Am J Clin Oncol, 16: 506-8.

Granville C A, Memmott R M, Gills J J, Dennis P A. (2006) Handicapping the race to develop inhibitors of the phosphoinositide 3-kinase/Akt/mammalian target of rapamycin pathway. Clin Cancer Res, 12:679-89.

Greene, T. W. and Wuts, P. G. M. "Protective Groups in Organic Synthesis" John Wiley & Sons, Inc. New York. 3rd Ed. pg. 819, 1999.

Hoffman K, Holmes F A, Fraschini G, et al. (1996) Phase I-II study: triciribine (tricyclic nucleoside phosphate) for metastatic breast cancer. Cancer Chemother Pharmacol., 37:254-8.

Honda, T. et al. *Bioorg. Med. Chem. Lett.,* 1997, 7:1623-1628.

Honda, T. et al. *Bioorg. Med. Chem. Lett.,* 1998, 8:2711-2714.

Honda, T. et al. *J. Med. Chem.,* 2000, 43:4233-4246.

Jetzt A, Howe J A, Horn M T, et al. (2003) Adenoviral-mediated expression of a kinase-dead mutant of Akt induces apoptosis selectively in tumor cells and suppresses tumor growth in mice. Cancer Res, 63:697-706.

Jiang K, Coppola D, Crespo N C, et al. (2000) The phosphoinositide 3-OH kinase/AKT2 pathway as a critical target for farnesyltransferase inhibitor-induced apoptosis. Mol Cell Biol, 20:139-48.

Jin X, Gossett D R, Wang S, et al. (2004) Inhibition of AKT survival pathway by a small molecule inhibitor in human endometrial cancer cells. Br J Cancer, 91:1808-12.

Jones P F, Jakubowicz T, Pitossi F J, Maurer F J, Hemmings B A. (1991a) Molecular cloning and identification of a serine/threonine protein kinase of the second-messenger subfamily. Proc Natl Acad Sci USA, 88:4171-5.

Jones P F, Jakubowicz T, Hemmings B A. (1991b) Molecular cloning of a second form of rac protein kinase. Cell Reg, 2:1001-9.

Kondapaka S B, Singh S S, Dasmahapatra G P, Sausville E A, Roy K K. (2003) Perifosine, a novel alkylphosphoiipid, inhibits protein kinase B activation. Mol Cancer Ther, 2:1093-103.

Konishi H, Kuroda S, Tanaka M, et al. (1995) Molecular cloning and characterization of a new member of the Rac protein kinase family: association of the pleckstrin homology domain of three types of Rac protein kinase with protein kinase C subspecies and beta gamma subunits of G proteins. Biochem Biophys Res Commun, 216:526-34.

Konoike, T. et al. *J. Org. Chem.,* 1997, 62:960-966.

Lindsley C W, Zhao Z, Leister W H, et al. (2005) Allosteric Akt (PKB) inhibitors: discovery and SAR of isozyme selective inhibitors. Bioorg Med Chem Lett, 15:761-4.

Luo Y, Shoemaker A R, Liu X, et al. (2005) Potent and selective inhibitors of Akt kinases slow the progress of tumors in vivo. Mol Cancer Ther, 4:977-86.

Marsh Rde W, Rocha Lima C M, Levy D E, Mitchell E P, Rowland K M Jr, Benson A B $3^{rd}$. (2007) A phase II trial of perifosine in locally advanced, unresectable, or metastatic pancreatic adenocarcinoma. Am J Clin Oncol, 30:26-31.

Martin, E. W., 1995, Easton Pa., Mack Publishing Company, $19^{th}$ ed.

Meuillet E J, Ihle N, Baker A F, et al. (2004) In vivo molecular pharmacology and antitumor activity of the targeted Akt inhibitor PX-316. Oncol Res, 14:513-27.

Persad S, Attwell S. Gray V, et al. (2001) Regulation of protein kinase B/Akt-serine 473 phosphorylation by integrin-linked kinase: critical roles for kinase activity and amino acids arginine 211 and serine 343. J Biol Chem, 276:27462-9.

Sarbassoy D D, Guertin D A, Ali S M, Sabatini D M. (2005) Phosphorylation and regulation of Akt/PKB by the rictor-mTOR complex. Science, 307:1098-101.

Sato S, Fujita N, Tsuruo T. (2002) Interference with PDK1-Akt survival signaling pathway by UCN-01 (7-hydroxystaurosporine). Oncogene, 21:1727-38.

Solit D B, Basso A D, Olshen A B, Scher H I, Rosen N. (2003) Inhibition of heat shock protein 90 function down-regulates Akt kinase and sensitizes tumors to Taxol. Cancer Res, 63: 2139-44.

Stambolic V, Suzuki A, de la Pompa J L, et al. (1998) Negative regulation of PKB/Akt-dependent cell survival by the tumor suppressor PTEN. Cell, 95:29-39.

Sun J, Blaskovic M A, Knowles D. et al. (1999) Antitumor efficacy of a novel class of non-thiol-containing peptidomimetic inhibitors of farnesyltransferase and geranylgeranyltransferase I: combination therapy with the cytotoxic agents cisplatin, Taxol, and gemcitabine. Cancer Res, 59:4919-26.

Sum M, Wang C, Paciga J E, et al. (2001) AKT1/PKB☐ kinase is frequently elevated in human cancers and its constitutive activation is required for oncogenic transformation in NIH3T3 cells. Am J Path, 159:431-7.

Toker A and Newton A C. (2000) Akt/Protein kinase B is regulated by autophosphorylation at the hypothetical PDK-2 Site. J Biol Chem, 275:8271-4.

Van Ummersen L, Binger K, Volkman J, et al. (2004) A phase I trial of perifosine (NSC 639966) on a loading dose/maintenance dose schedule in patients with advanced cancer. Clin Caner Res, 10:7550-6.

Vazquez F, Sellers W R. (2000) The PTEN tumor suppressor protein: an antagonist of phosphoinositide 3-kinase signaling. Biochim Biophys Acta, 1470:M21-35.

West K A, Castillo S S and Dennis P A. (2002) Activation of the PI3K/Akt pathway and chemotherapeutic resistance. Drug Resist Updat, 5:234-48.

Wick M J, Dong L Q, Riojas R A, Ramos F J, Liu F. (2000) Mechanism of phosphorylation of protein kinase B/Akt by a constitutively active 3-phosphoinositide-(dependent protein kinase-1. J Biol Chem, 275:40400-6.

Xu W, Yuan X, Jung Y J, et al. (2003) The Heat Shock Protein 90 inhibitor Geldanamycin and the ErbB inhibitor ZD1839 promote rapid PP1 phosphatase-dependent inactivation of AKT in ErbB2 overexpressing breast cancer cells. Cancer Res, 63:7777-84.

Yang L, Dan H C, Sun M, et al. (2004) Akt/protein kinase B signaling inhibitor-2, a selective small molecule inhibitor of Akt signaling with antitumor activity in cancer cells overexpressing Akt. Cancer Res, 64:4394-9.

Yang W L, Roland I H, Godwin A K, Xu X X. (2005) Loss of TNF-alpha-regulated COX-2 expression in ovarian cancer cells. Oncogene, 24:7991-8002.

We claim:

1. A method for inhibiting the Akt/PKB pathway in a cancer cell in which said pathway is present, wherein said cell constitutively expresses an Akt protein or said cell expresses elevated levels of an Akt protein, said method comprising contacting the cell with an effective amount of a compound according to formula (I):

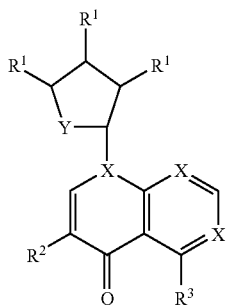

(I)

wherein

X is N;

Y is O, NH, or S;

R¹ is, independently, —H, —OH, —NH₂, —NO₂, halogen, alkyl optionally substituted with —OH, or alkoxy optionally substituted with —OH;

R² is —C(O)NH₂ or alkoxy optionally substituted with —OH, halogen, alkyl, or alkoxy;

R³ is —OH, —NH₂, —C(O)NH₂, or alkoxy optionally substituted with —OH, halogen, alkyl, or alkoxy; or a pharmaceutically acceptable salt thereof;

or a composition comprising said compound.

2. The method according to claim 1, wherein the compound is administered intravenously or intranasaly; and the effective amount of the compound of formula (I) is 0.01 to about 20 mg/kg of body weight; or the compound is administered intraperitonealy, subcutaneously, or intramuscularly; and the effective amount of the compound of formula (I) is 0.01 to about 100 mg/kg of body weight; or the compound is administered orally; and the effective amount of the compound of formula (I) is 0.01 to about 200 mg/kg of body weight.

3. The method of claim 1, wherein each X is N or Y is O.

4. The method of claim 1, wherein each R¹ is independently —OH or —CH₂OH.

5. The method of claim 1, wherein R² is —C(O)NH₂.

6. The method of claim 1, wherein the compound is API-1.

7. The method of claim 1, wherein the compound is according to formula (II):

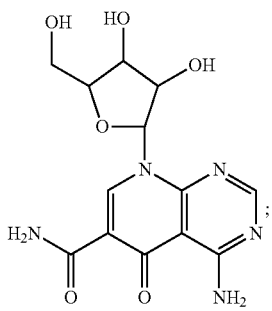

(II)

or a pharmaceutically acceptable salt thereof.

8. The method of claim 1, wherein the compound is according to the following formula:

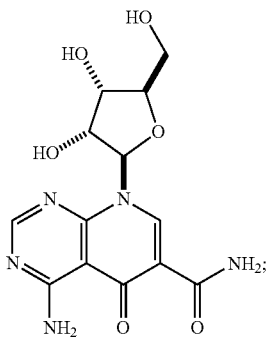

or a pharmaceutically acceptable salt thereof.

9. A method for inhibiting the Akt/PKB pathway in a malignant tumor cell in which said pathway is present, wherein said cell constitutively expresses an Akt protein or said cell expresses elevated levels of an Akt protein, said method comprising contacting the cell with an effective amount of a compound according to formula (I):

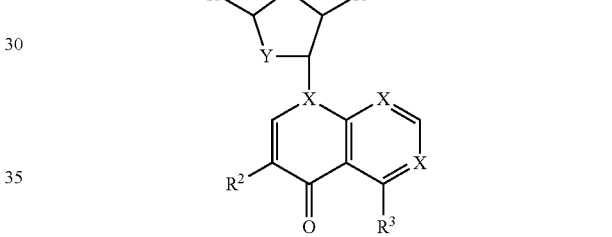

(I)

wherein

X is N;

Y is O, NH, or S;

R¹ is, independently, —H, —OH, —NH₂, —NO₂, halogen, alkyl optionally substituted with —OH, or alkoxy optionally substituted with —OH;

R² is —C(O)NH₂ or alkoxy optionally substituted with —OH, halogen, alkyl, or alkoxy;

R³ is —OH, —NH₂, —C(O)NH₂, or alkoxy optionally substituted with —OH, halogen, alkyl, or alkoxy; or a pharmaceutically acceptable salt thereof;

or a composition comprising said compound.

10. The method according to claim 9, wherein the compound is administered intravenously or intranasaly; and the effective amount of the compound of formula (I) is 0.01 to about 20 mg/kg of body weight; or the compound is administered intraperitonealy, subcutaneously, or intramuscularly; and the effective amount of the compound of formula (I) is 0.01 to about 100 mg/kg of body weight; or the compound is administered orally; and the effective amount of the compound of formula (I) is 0.01 to about 200 mg/kg of body weight.

11. The method of claim 9, wherein each X is N or Y is O.

12. The method of claim 9, wherein each R¹ is independently —OH or —CH₂OH.

13. The method of claim 9, wherein R² is —C(O)NH₂.

14. The method of claim 9, wherein the compound is API-1.

15. The method of claim 9, wherein the compound is according to formula (II):
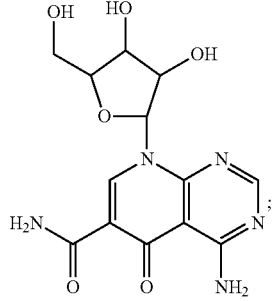
(II)
or a pharmaceutically acceptable salt thereof.
16. The method of claim 9, wherein the compound is according to the following formula:
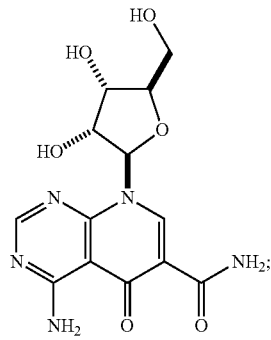
or a pharmaceutically acceptable salt thereof.
* * * * *